(12) United States Patent
O'Driscoll et al.

(10) Patent No.: US 8,634,928 B1
(45) Date of Patent: Jan. 21, 2014

(54) WIRELESS POWER TRANSMISSION FOR IMPLANTABLE MEDICAL DEVICES

(75) Inventors: Stephen O'Driscoll, Menlo Park, CA (US); Ada Shuk Yan Poon, San Leandro, CA (US); Teresa H. Meng, Saratoga, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 967 days.

(21) Appl. No.: 12/485,641

(22) Filed: Jun. 16, 2009

(51) Int. Cl.
*A61N 1/00* (2006.01)
(52) U.S. Cl.
USPC .................................. 607/61; 607/33; 607/60
(58) Field of Classification Search
USPC ................................. 607/33, 61, 60
See application file for complete search history.

(56) References Cited

U.S. PATENT DOCUMENTS

| | | | | |
|---|---|---|---|---|
| 6,809,701 | B2 * | 10/2004 | Amundson et al. | 343/873 |
| 7,409,245 | B1 * | 8/2008 | Larson et al. | 607/36 |
| 2007/0129767 | A1 * | 6/2007 | Wahlstrand | 607/33 |
| 2010/0045114 | A1 * | 2/2010 | Sample et al. | 307/104 |
| 2011/0004278 | A1 * | 1/2011 | Aghassian et al. | 607/61 |

OTHER PUBLICATIONS

Ada S.Y. Poon, et al., "Optimal Frequency for Wireless Power Transmission into Dispersive Tissue", Annual International Conference of the IEEE Engineering in Medicine and Biology Society, Lyon, France, Aug. 2007, pp. 1-12.
Stephen O'Driscoll, et al., "Neurons to Silicon: Implantable Prosthesis Processor", Silicon for Biology, IEEE International Solid-State Circuits Conference, Stanford University, Feb. 8, 2006, Section 30.1.

* cited by examiner

*Primary Examiner* — George Manuel
*Assistant Examiner* — William Levicky
(74) *Attorney, Agent, or Firm* — Pillsbury Winthrop Shaw Pittman LLP

(57) ABSTRACT

Described is an apparatus and method for increasing a gain of a transmitted power signal in a wireless link when operating in a mid field wavelength that is within a range between wavelength/100 to 100*wavelength and within a medium having a complex impedance between a transmit antenna and a receive antenna. The apparatus and method maximize the gain in the wireless link using simultaneous conjugate matching, to increase power transfer within the transmitted power signal, wherein the simultaneous conjugate matching accounts for interaction between the transmit antenna and the receive antenna, including the complex impedance of the medium between the transmit antenna and the receive antenna.

14 Claims, 19 Drawing Sheets

Advantages of Radiating Near Field

|  | Near Field | Far Field | Radiating Near Field |
|---|---|---|---|
| Gain | $\dfrac{1}{d^6}$ | $\dfrac{1}{d^2}$ | $\dfrac{1}{d^3}$ |
| Range | $\ll \lambda$ | $\gg \lambda$ | $\sim \lambda$ |
| Frequency | Low (1-10 MHz) | High | Relative High (.3 - 3 GHz) |
| Alignment | Sensitive | Insensitive | Relatively Insensitive |
| Spatial Patterning | No | Yes | Yes |
| Implicit Feedback | Yes | No | Yes |
| External Power Source | Yes | No | Yes |

FIG. 6

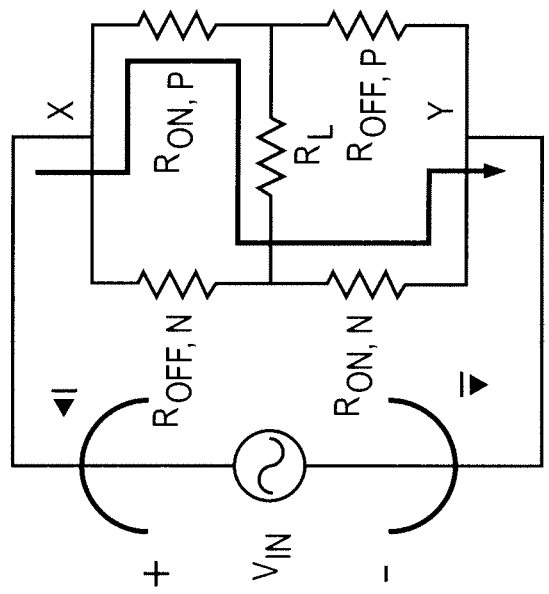
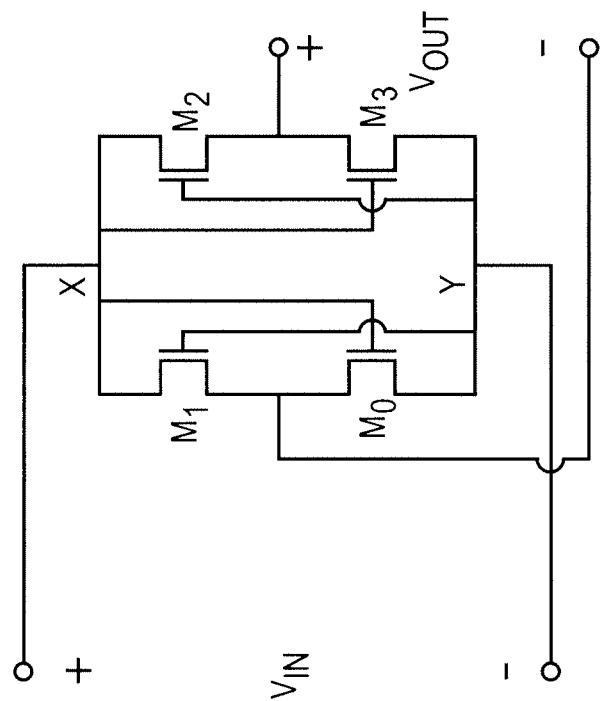
FIG. 18A
FIG. 18B

WIRELESS POWER TRANSMISSION FOR IMPLANTABLE MEDICAL DEVICES

BACKGROUND

Implantable medical devices (IMDs) are a rapidly growing area of technology. In-vivo monitoring and treatment of key biological parameters can greatly assist in managing health and preventing disease. IMDs are complete systems often incorporating signal transducers, wireless data transceivers and signal processing circuits. Power consumption in these devices requires batteries, which must be replaced periodically, or inductive power coupling antennae, both of which dominate device volume, increasing patient discomfort and severely restricting the range of viable applications.

Previous inductive powering links for IMDs operate in the low MHz requiring loop antenna diameters of a few cm and near-perfect transmitter and receiver alignment to deliver sufficient power. This choice of frequency is usually explained by saying that tissue losses become too large at higher frequencies and referring to a qualitative analysis. For these low MHz inductively coupled links the range is much less than a wavelength and thus the links satisfy the near field approximation to Maxwell's equations. Therefore resonant tuning techniques can be used to achieve the maximum energy transfer from the source to the load circuits for these links. Inductive coupling antennae of this size are viable for retinal implants where there is an existing cavity in the eye-socket but are much too large for many other IMDs such as implantable glucose sensors.

The physics behind wireless powering is described first. A time-varying current is set up on the transmit antenna. This gives rise to a time-varying magnetic field. The time-varying magnetic field, in turn, gives rise to an electric field. The electric field induces a current on the receive antenna. Then, this induced current on the receive antenna intercepts the incident electric field and/or magnetic field from the transmit antenna, and generates power at the receiver. Prior devices for wireless transmission of power to medical implants mainly operate based on inductive coupling over the near field in conjunction with a few based on electromagnetic radiation over the far field.

Devices based on inductive coupling operate at very low frequency, 10 kHz to 1 MHz. A wavelength is long relative to the size of the transmit and receive antennas. They are usually a few cm in diameter. Most energy stored in the field generated by the transmit antenna is reactive, that is, the energy will go back to the transmitter if there is no receiver to intercept the field. The separation between transmit and receive antennas is very small, usually a few mm. The low frequency and the short separation mean that there is apparently no phase change between the field at the transmitter and the incident field at the receiver. The increase in the transmit power due to the presence of the receiver mostly delivers to the receiver, like a transformer. Prior devices are therefore designed using the transformer model where various tuning techniques are proposed.

To deliver sufficient power to the implant using inductive coupling based devices, the receive antenna attached to the implant is of a few cm in diameter which is too large. It is required to be in close proximity to the transmit antenna on the external device. The power link is very sensitive to misalignment between the antennas. For example, some devices use a magnet to manually align them.

Devices based on electromagnetic radiation operate at much higher frequency, 0.5 GHz to 5 GHz. Transmit and receive antennas are on the order of a wavelength. For example, a wavelength is 12.5 cm at 2.4 GHz. Therefore, transmit and receive antennas are usually at least a few cm in diameter which is of similar size to those devices based on inductive coupling. As the transmit antenna is comparable to a wavelength, radiated power dominates. The receive antenna is in the far field of the transmit antenna and captures a very small fraction of the radiated power. That is, most of the transmit power is not delivered to the receiver. The link efficiency is very low. In return, the distance between the transmit antenna and the tissue interface is farther, a few cm to 10's of cm, the depth of the implant inside the body is larger, 1 cm to 2 cm, and the link is insensitive to misalignment between antennas. Prior devices are designed using independent transmit and receive matching networks.

The above two prior approaches have a common disadvantage: they require large receive antennas, 1 cm to a few cm. The paper by Poon et al. titled "Optimal Frequency for Wireless Power transmission over Dispersive Tissue" showed that small receive antenna is feasible. The authors show that the optimal transmission frequency for power delivery over lossy tissue is in the GHz-range for small transmit and small receive antennas (a few mm in diameter.) The optimal frequency for larger transmit antenna (a few cm in diameter) and small receive antenna is in the sub-GHz range. That is, the optimal frequencies are in between 0.5 GHz and 5 GHz. Compared with the frequency used in prior devices based on inductive coupling, the optimal frequency is about 2 orders of magnitude higher. For a fixed receive area, the efficiency can be improved by 30 dB which corresponds to a 10 times increase in the implant depth, from a few mm to a few cm. For a fixed efficiency, the receive area can be reduced by 100 times, from a few cm to a few mm in diameter. When the transmit antenna is close to the tissue interface, the separation between the transmit and the receive antenna approximately equals the implant depth. Inside the body, the wavelength is reduced. For example, a wavelength inside muscle is 1.7 cm at 2.4 GHz. Consequently, the transmit-receive separation is on the order of a wavelength. The device operates neither in the near field nor in the far field. It operates in the mid field. Furthermore, the transmit dimension of a few cm will be comparable to a wavelength.

SUMMARY

The inventions described herein present apparatus and methods to deliver power wirelessly from an external device using an antenna or an antenna array to an implant.

Multiple antennas can be used in the external device to maximize the power transfer efficiency. The use of multiple transmit antennas also reduces the sensitivity of the power link to the displacement and orientation of the receive antenna.

These inventions as described can provide one or more of the following advantages: smaller antenna size; greater transfer distance inside body; and reduced sensitivity to misalignment between transmit and receive antennas, as the link gain is increased through choice of frequency, matching, and beam forming which requires the ability to locate the receiver.

These inventions also provide a novel method to achieve feedback of information from the internal device to the external device about the location of the internal device and properties of the medium in between. Conventional techniques require explicit feedback of information from the internal device to the external device. The present invention achieves implicit feedback by exploiting the fact that the internal device is close to the external device, and therefore the external device should be able to sense the presence of the internal device and properties of the medium in between.

In one aspect there is provided apparatus and methods for applying simultaneous conjugate matching to wireless links.

In another aspect is provided adaptive tuning of that simultaneous conjugate matching.

In a particular embodiment, the apparatus and methods operate with wireless power signals in the sub-GHz or the GHz-range, more specifically, in between 0.5 GHz and 5 GHz.

In a particular aspect, there is provided apparatus and methods for increasing a gain of a transmitted power signal in a wireless link when operating in a mid field wavelength that is within a range between wavelength/100 to 100*wavelength and within a medium having a complex impedance between a transmit antenna and a receive antenna. The apparatus and methods maximize the gain in the wireless link using simultaneous conjugate matching, to increase power transfer within the transmitted power signal, wherein the simultaneous conjugate matching accounts for interaction between the transmit antenna and the receive antenna, including the complex impedance of the medium between the transmit antenna and the receive antenna.

In another aspect is provided apparatus for wireless power transmission within an environment of unknown transmission characteristics comprising: a wireless power transmitter, the wireless power transmitter including: an adaptive match transmit circuit with a tunable impedance, which supplies a tunable impedance to a power signal having a frequency of at least 0.5 GHZ; and a wireless transmitter; and a wireless power receiver, the wireless power receiver including: a receive antenna configured to receive the transmitted power signal as a received power signal; an adaptive match receive circuit, wherein the adaptive match receive circuit receives the received power signal, and is configured to match the tunable impedance, in dependence upon the environment of unknown transmission characteristics, to thereby increase a gain of the received power signal.

In a particular aspect the adaptive match receive circuit provides a feedback signal to the adaptive match transmit circuit, wherein the feedback signal provides an indication of a gain of the power signal as received at the wireless power transmitter for a particular tuned impedance.

BRIEF DISCUSSION OF THE DRAWINGS

These and other aspects and features of the present invention will become apparent to those of ordinary skill in the art upon review of the following description of specific embodiments of the invention in conjunction with the accompanying figures, wherein:

FIG. 6 shows advantages of using radiating near field according to the present invention as contrasted to near field and far field.

Figure 19:
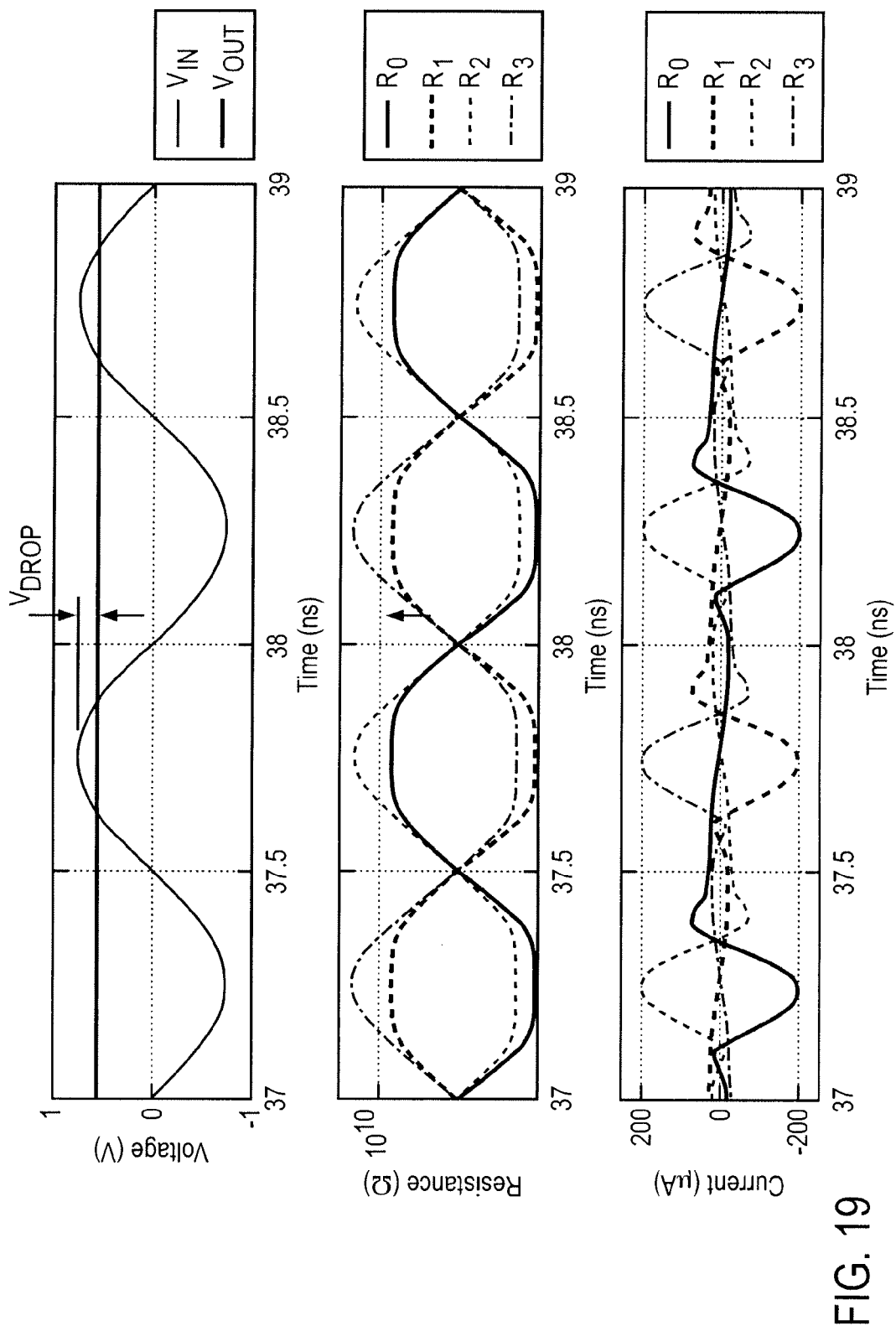
Figure 20:
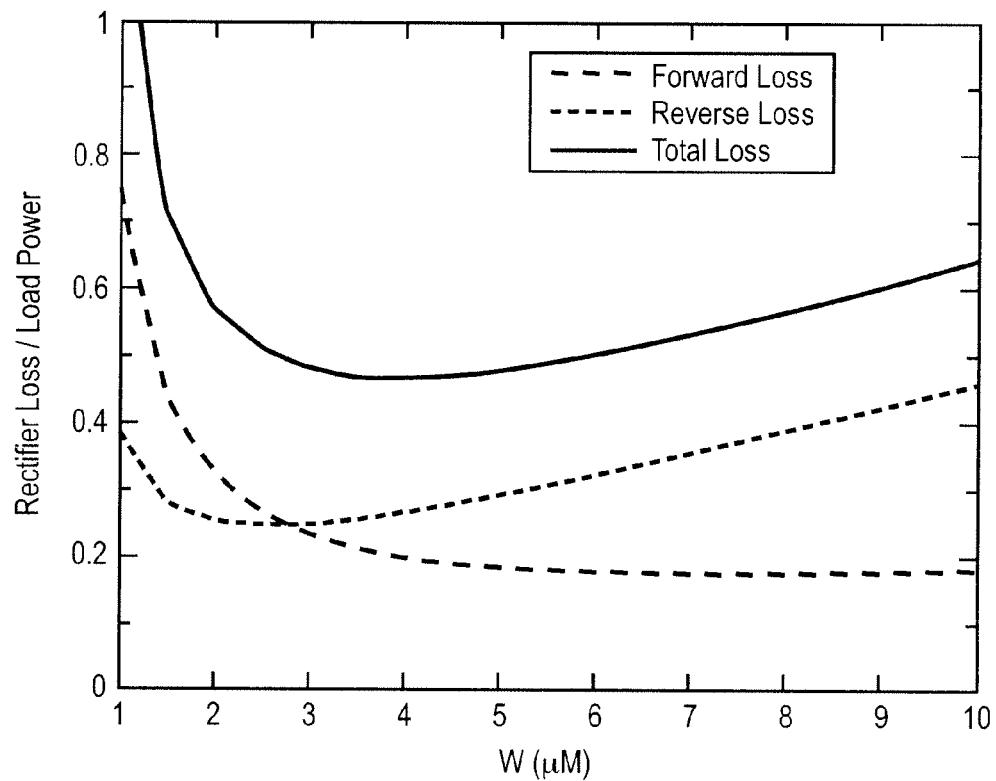
Figure 21:
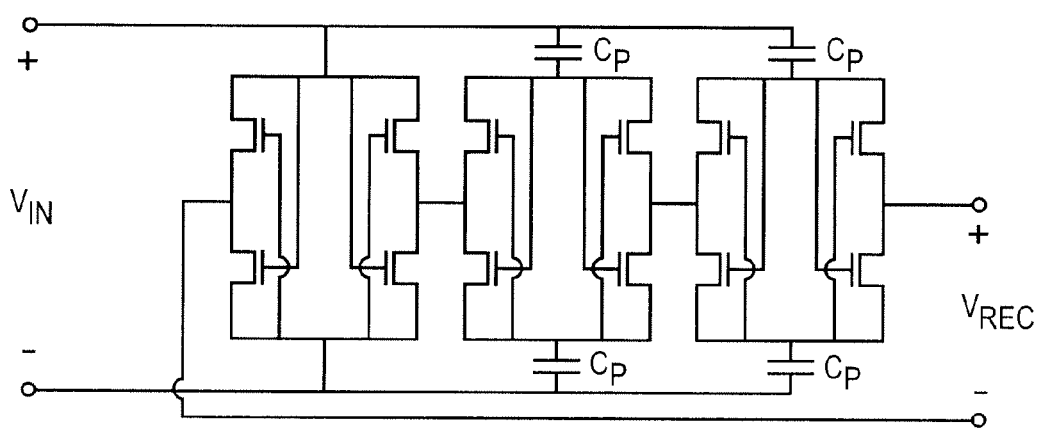
Figure 22:
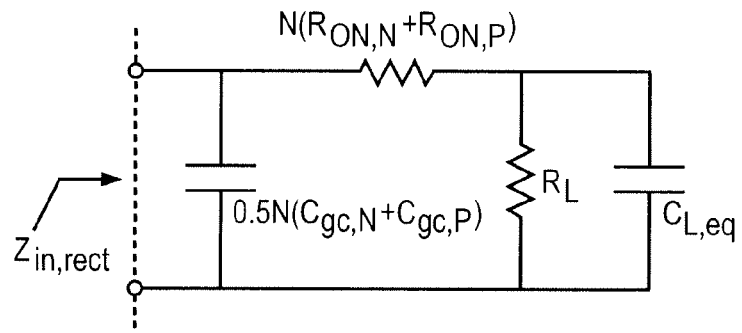
Figure 23:
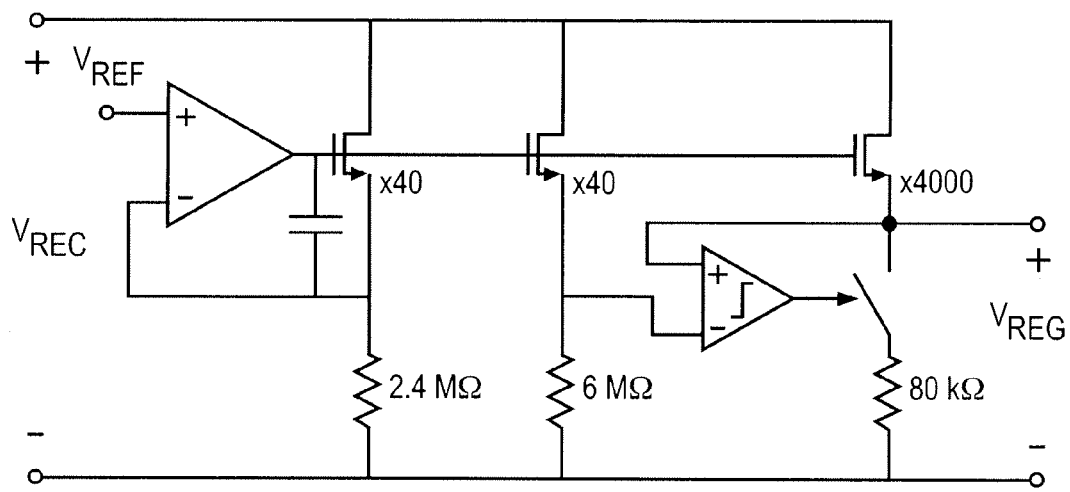
Figure 24:
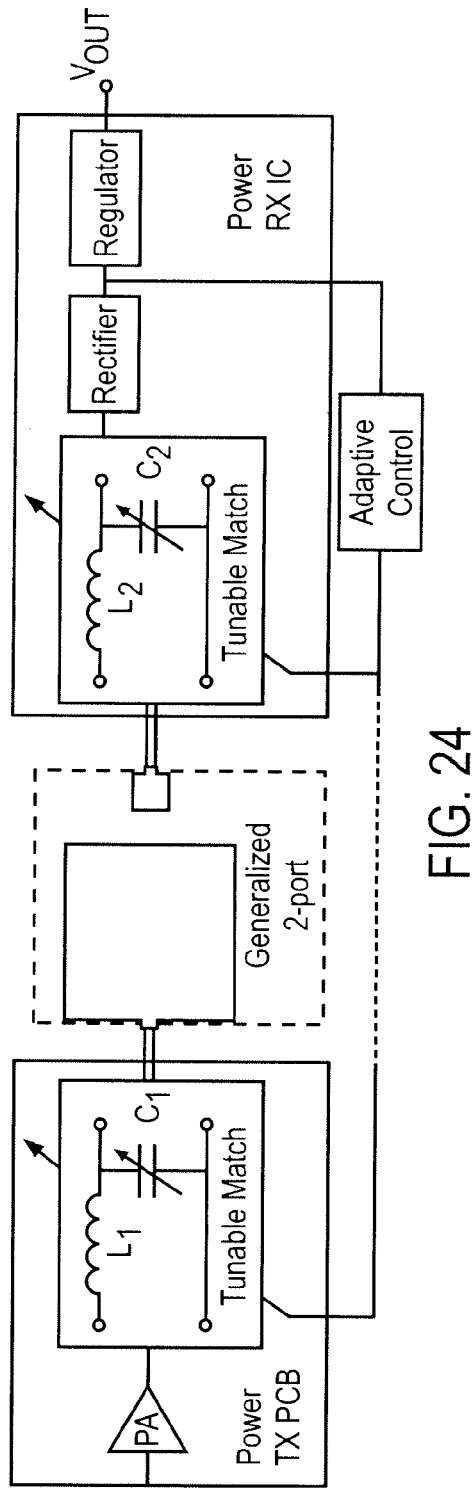
Figure 25:
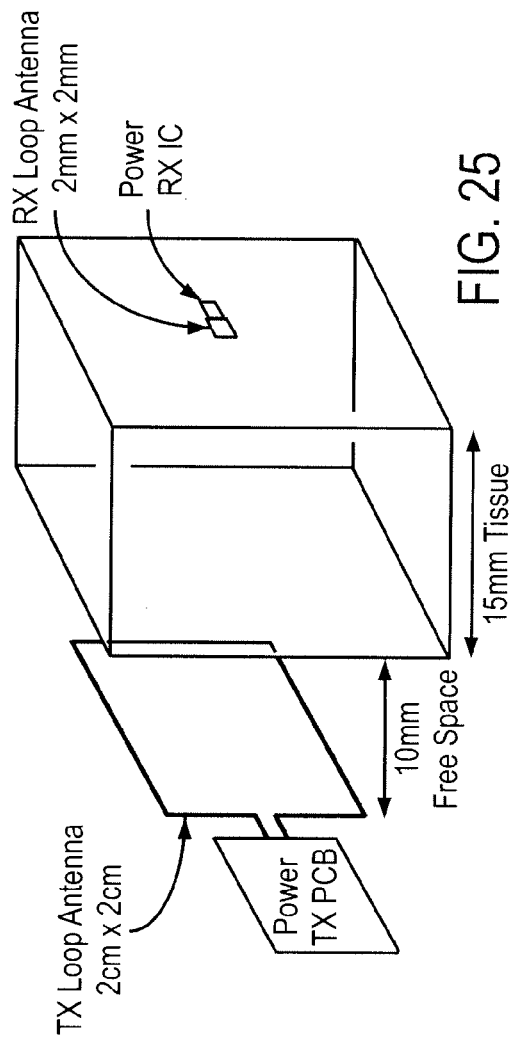
Figure 26:
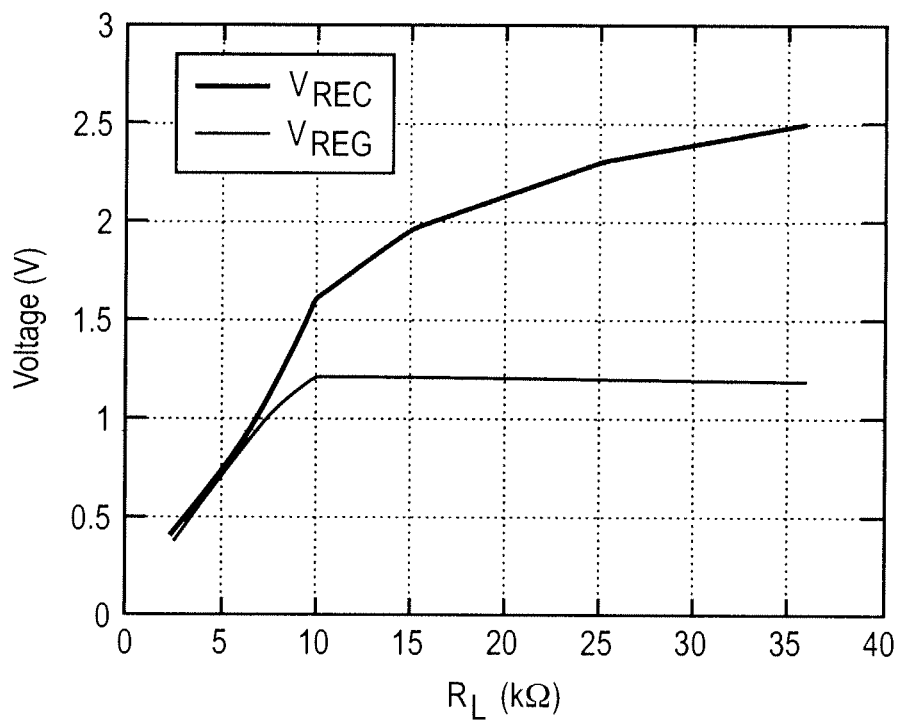
Figure 27:
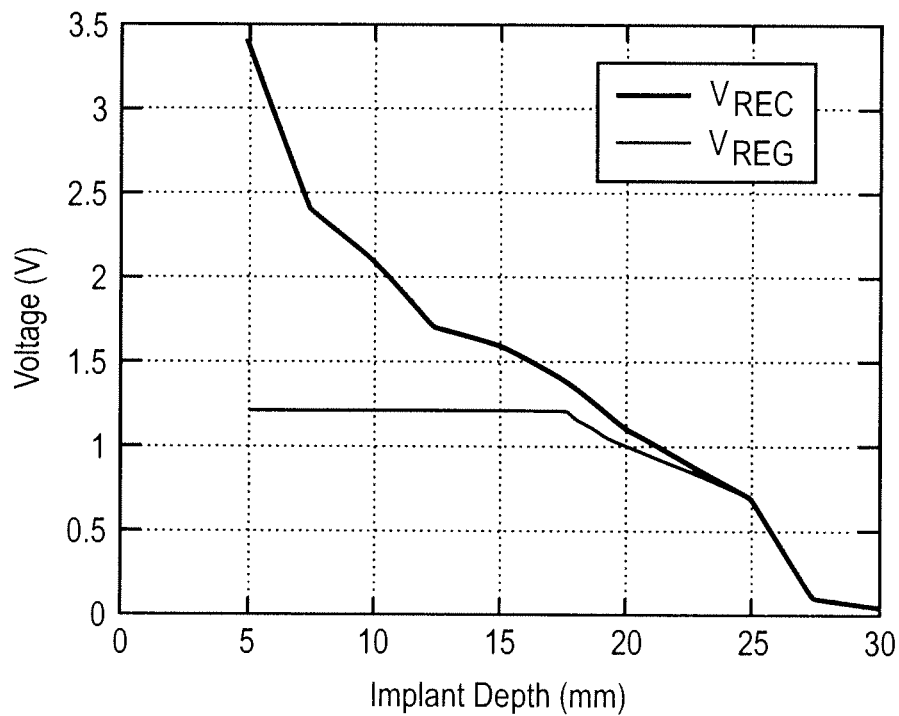

FIGS. 18a-b show a synchronous self-driven rectifier and an equivalent model of voltage dependent resistances;

FIG. 19 shows various currents;

FIG. 20 shows a slice of a curve that represents a ratio of loss in the rectifier to power delivered to the load versus widths of NMOS and PMOS devices;

FIG. 21 shows an embodiment of a synchronous self-driven rectifier with pump capacitances;

FIG. 22 shows an input impedance model;

FIG. 23 illustrates an embodiment of a series regulator that incorporates two replica bias stages;

FIG. 24 shows an embodiment of the system;

FIG. 25 shows two antennae according to the system axially aligned with muscle tissue therebetween;

FIG. 26 shows a plot of rectifier and regulator output voltages versus load impedance as the load impedance was varied; and FIG. 27 shows a plot of rectifier and regulator output voltages versus implant depth for a particular load impedance.

DETAILED DESCRIPTION OF THE PREFERRED EMBODIMENTS

The present method is directed to wireless power transmission for implantable medical devices, and uses the recognition that high frequencies can penetrate liquids and biological tissue, and that the optimal operating frequency is a function of the depth of the receive inside the body. Thus, receive antennas as small as 2 mm$^2$ can deliver substantial power.

Figure 1:
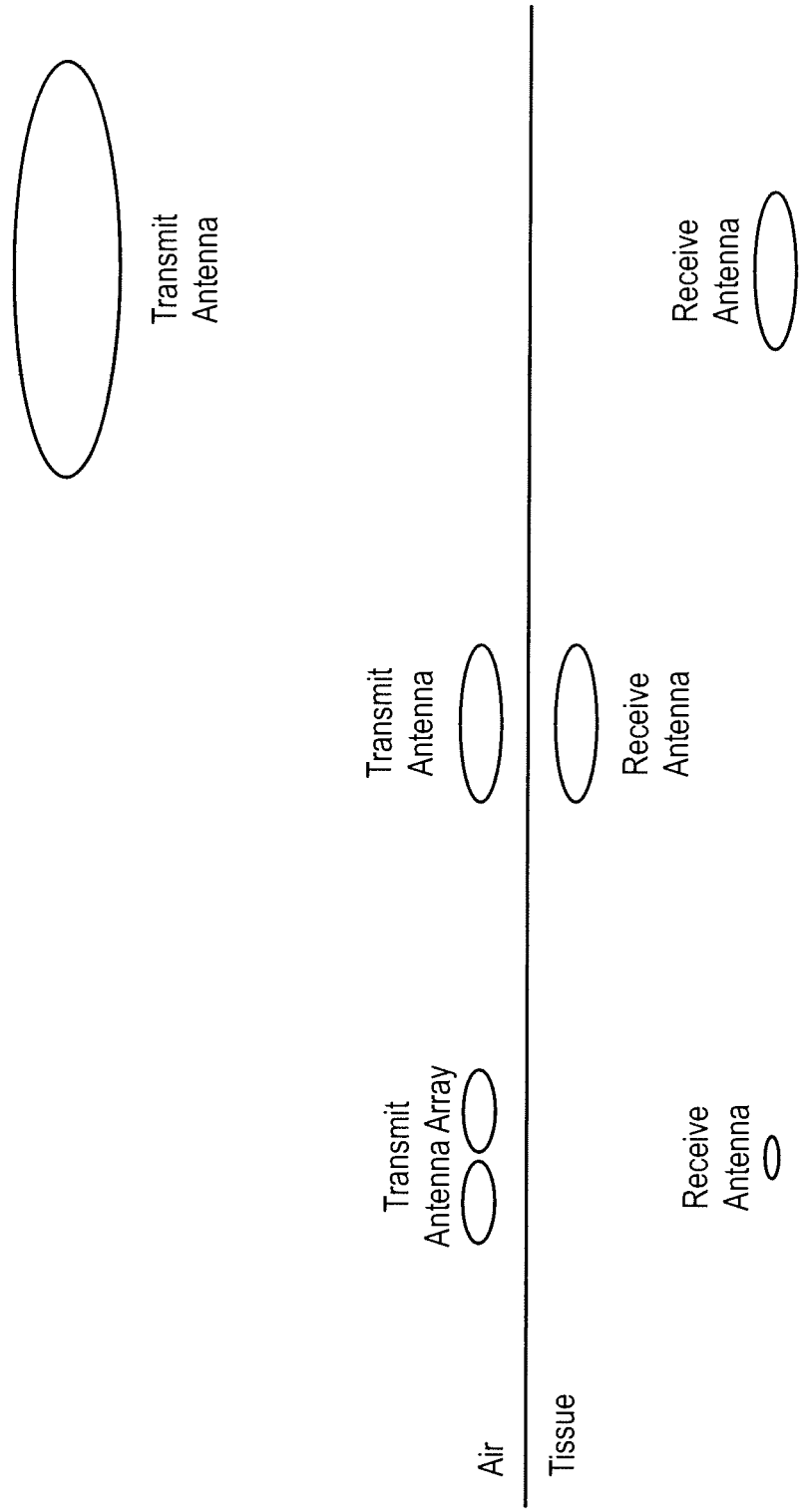
FIG. 1a illustrates relative size of the transmit and receive antennas as compared conventional transmit and receive antennas illustrated in FIGS. 1b-1c.

The present method is able to achieve the same or better efficiency as devices based on inductive coupling while the receive antenna on the implant is smaller and deeper inside the body, as illustrated in FIG. 1A and FIG. 1B. It achieves the miniaturization in the receive antenna and the extension in the transfer distance by operating in the sub-GHz or the GHz-range, more specifically, in between 0.5 GHz and 5 GHz, in a manner that provides a power-free wireless link for implants, and for battery-less implanted medical sensors.

At such high frequency, the wavelength inside body is small. As the transmit antenna is placed close to the tissue interface, we can use this wavelength as the reference wavelength for the design of the transmit antenna. This wavelength is about 6 times smaller than the corresponding wavelength in air at the same frequency. The present invention, therefore, exploits wireless power delivery and data link circuits, described hereinafter, that are magnitudes smaller than conventional devices, and also can provide significantly greater transfer distance for high margin and high volume medical applications Multiple antennas can also be used in the external device to maximize the power transfer efficiency. The use of multiple transmit antennas also reduces the sensitivity of the power link to the displacement and orientation of the receive antenna. In devices based on electromagnetic radiation, the use of multiple transmit antennas is less effective due to the much longer wavelength in air. Also, the receive antennas in this invention are much smaller than those in electromagnetic radiation, as illustrated in FIG. 1A and FIG. 1C. This, the present invention can provide one or more of the following advantages: smaller antenna size; greater transfer distance inside body; and reduced sensitivity to misalignment between transmit and receive antennas, as the link gain is increased through choice of frequency, matching, and beam forming which requires the ability to locate the receiver. All of those techniques and their preferred embodiments are described to the level that a person of ordinary skill in the art could implement them.

This invention provides a novel method to achieve feedback of information from the internal device to the external device about the location of the internal device and properties of the medium in between. Conventional techniques require explicit feedback of information from the internal device to the external device. The present invention achieves implicit feedback by exploiting the fact that the internal device is close to the external device, and therefore the external device should be able to sense the presence of the internal device and properties of the medium in between. That is, the present invention does not require the explicit feedback of information from the internal device to the external device in order to adapt to the changing location of the internal device and the changing properties of the medium in between.

The present invention can be applied to any device that is powered remotely, particularly to those devices in which having to align the external and the internal antennas is undesirable. All systems and devices which utilize electric power for any purpose, including but not limited to sensing; control; actuating; processing; authenticating; lighting; and heating, could potentially benefit from this invention and where there is potential benefit in having the power source at a remote location e.g. a medical implant in which a battery can not be placed due to device size limitations and/or those systems which require two-way communication in which there is potential benefit in having the power source at a remote location. This invention should be used both as a stand-alone product and as a sub-component in larger systems.

Figure 2:
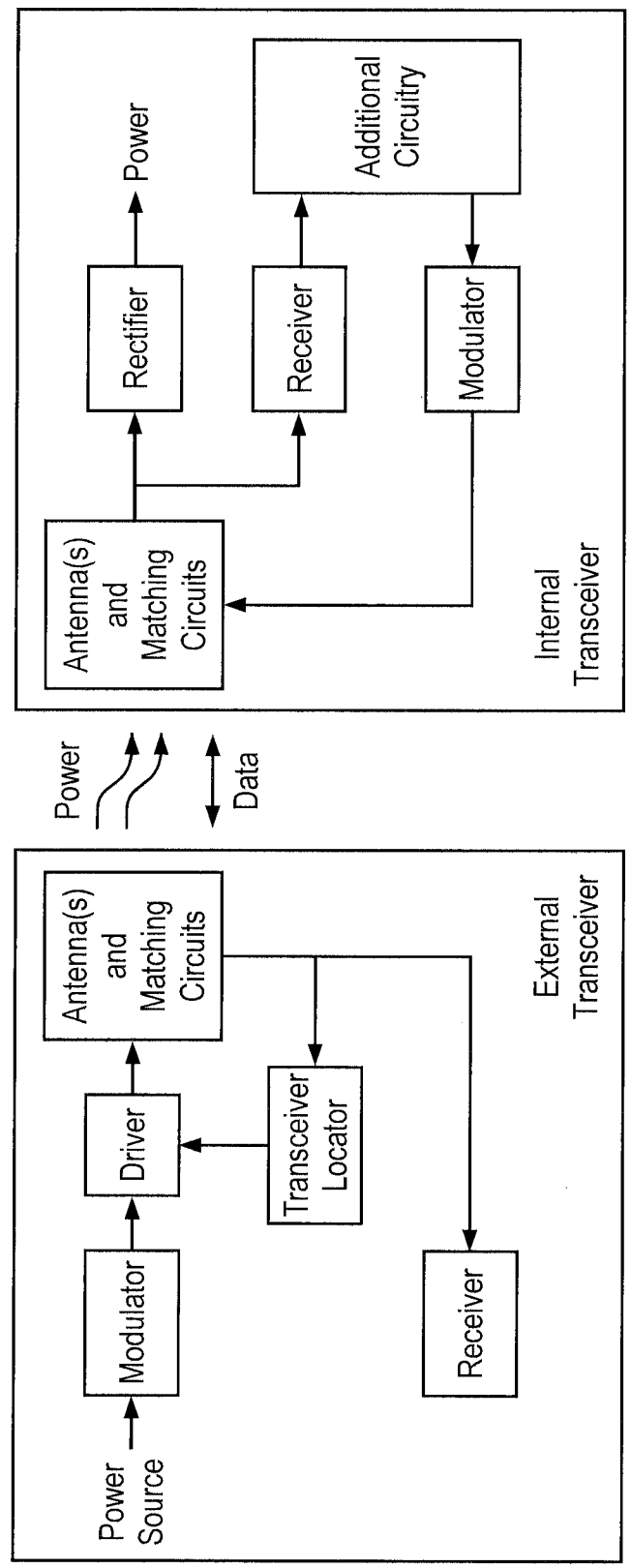
FIG. 2 illustrates a block diagram of an external transceiver and internal transceiver according to one embodiment.

FIG. 2 illustrates one embodiment of the present invention. A power source connected to electronic circuits and an antenna (or antennas), herein referred to as the external transceiver, transmits power wirelessly to a remote antenna (or antennas) and the electronic circuits they are connected to, herein referred to as the internal transceiver. The external transceiver includes: (1) a driver which takes information from the transceiver locator to provide RF signals to the antenna(s) and matching in such a way that power and data are wirelessly transferred to the internal transceiver with reduced sensitivity to the misalignment between antenna (or antennas) on the external transceiver and that (or those) on the internal transceiver; (2) antenna(s) and matching when driven by the driver generates the intended electromagnetic field; (3) a transceiver locator which senses signals from the antenna(s) and matching, and uses those signals to determine the important aspects of the location of the internal transceiver and the medium in between; (4) a modulator which modifies the waveform of the power source to encode data that is sent to the internal transceiver; and (5) a receiver which extracts data from signals sensed at the antenna(s) and matching and the data is sent from the internal transceiver. The internal transceiver includes (1) antenna(s) and matching which produce voltage and current to power the remainder of the transceiver from the field generated by the external transceiver; (2) a rectifier which converts the high frequency energy to DC; (3) a receiver which extracts data sent from the external transceiver; (4) a modulator which encodes data sent to the external transceiver either implicitly or explicitly; and (5) additional circuitry as required by the applications.

The antenna(s) and matching of the preferred embodiment functions to maximize the power transfer from the driver at the external transceiver to the rectifier at the internal transceiver. In a first variation the matching views the link as an n-port network (in the microwave circuits sense) and provides simultaneous conjugate matching between those ports and the impedances of their source/load circuits. In a second variation the matching system is the same as the first except that the matching components are adaptively varied to achieve the maximum power transfer, and thus can adapt to varying range and tissue dielectrics. In a first preferred realization of the second variation the matching networks are L-networks realized from binary weighted arrays of capacitors and inductors whose value may be chosen according to the adaptive algorithm, in this variation the steepest descent algorithm is used.

The transceiver locator of the preferred embodiment functions to sense signals from the antenna(s) and matching and uses those signals to deteiinine the important aspects of the location of the internal transceiver, and properties of the medium in between the external and the internal transceivers.

Figure 3:
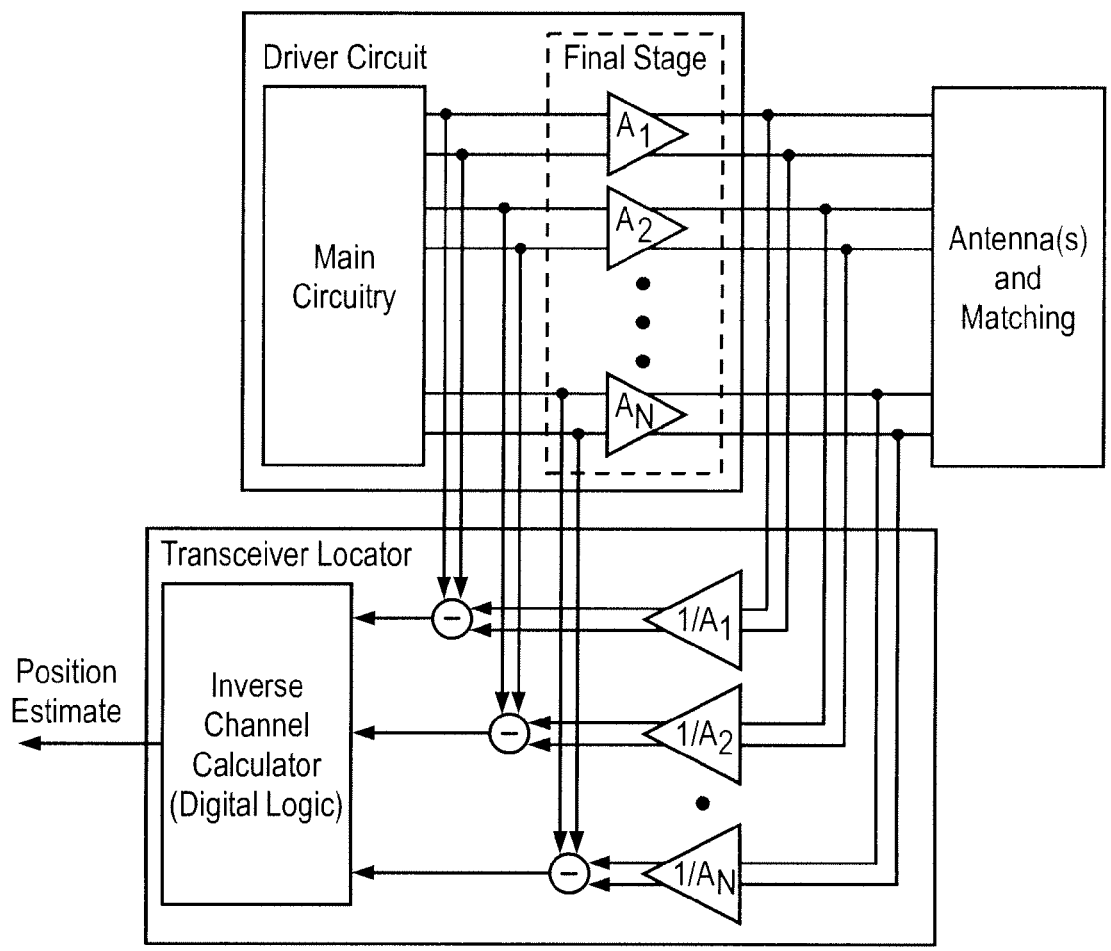
FIG. 3 illustrates a transceiver locator according to an embodiment.

The first variation of the transceiver locator operates by (1) finding the backscattered signal by subtracting the driver signals prior to the final stage from the signals observed at the antennas and matching input ports attenuated by the corresponding gains in the driver final stage, and (2) computing a channel inversion algorithm which takes that backscattered signal as input and gives the location estimate as output, as illustrated in FIG. 3. In a first preferred embodiment that attenuation is performed using amplifiers whose gain is chosen to be the inverse of the gain of the final stage amplifiers in the driver circuitry.

A second variation of the transceiver locator operates the same as the first variation except that the backscattered signal is found by amplifying the driver signals by the corresponding gains in the driver final stage in a second gain path and subtracting those amplified signals from the signals observed at the antennas and matching input ports (without any attenuation).

Figure 4:
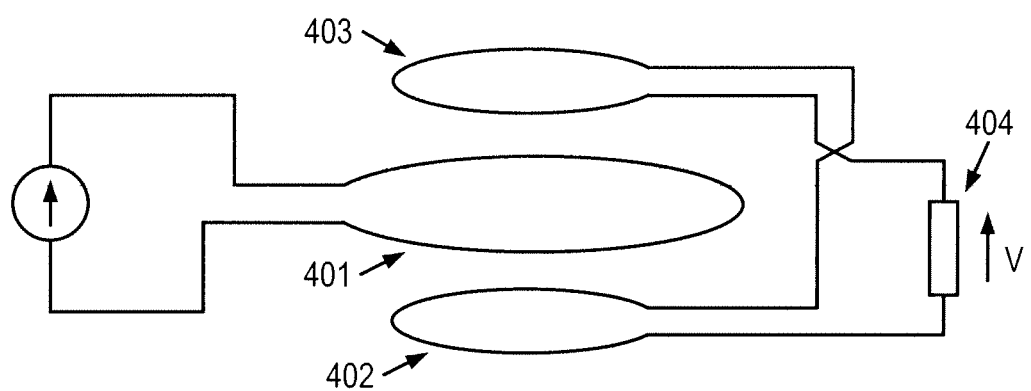
FIG. 4 illustrates a transceiver locator according to another embodiment.

A third variation of that transceiver locator operates the same as the variation first except that the backscattered signal is found using a differential antenna configuration at the external transceiver, as illustrated in FIG. 4. 401 is the transmit antenna, or one of the transmit antennas when multiple antennas are used. 402 and 403 are a pair of sensing antennas that are symmetrically placed with respect to the transmit antenna 401. The sensing antennas are connected in series-opposition. Therefore, the voltage measured across 404 is invariant to the driver signal on the transmit antenna, and gives the backscattered signal.

The driver of the preferred embodiment functions to supply the input signals to each port of the external transceiver's antenna(s) and matching network in such a way that power and data are wirelessly transferred to the internal transceiver with reduced sensitivity to the misalignment between the internal and the external antennas. The driver includes a digitally implemented algorithm, which takes the transceiver location estimate and uses it to choose the amplitude and phase of the signal driving each port.

The modulator at the internal transceiver of the preferred embodiment can operate as described in the following, although other implementations and variations can be used as well. The two preferred embodiments are: (1) encoding data by varying the impedance of the internal transceiver as seen by the external transceiver; or (2) explicitly transmitting a waveform and encoding data by varying the phase, amplitude, or frequency of the waveform.

The receiver at the external transceiver of the preferred embodiment performs its function according to the modulation schemes used by the internal transceiver. When the internal transceiver encodes data by varying its impedance, the receiver at the external transceiver can use either load modulation or backscatter modulation depending on the sensitivity of the receiver to measure the change in voltage and the change in reflected power.

EXAMPLES

This example considers the power transfer efficiency between a square transmit coil of width 2 cm and a square receive coil of width 2 mm. The transmit coils is 1 cm above the tissue interface. The tissue is modeled as a multi-layer medium. The upper layer is a 2-mm thick skin, the second layer is a 8-mm thick fat, and the lower layer is muscle. The receive coil is placed inside the muscle at a distance of 3 cm from the transmit coil. The dielectric properties of the tissue are obtained from the measurement reported in "The dielectric properties of biological tissues: III parametric models for the dielectric spectrum of tissues." Under the safety requirement of no more than 1.6 mW of power absorbed by any 1 g of tissue, the system can deliver 100 μW of power to the internal receiver which is sufficient for the operation of many applications.

Figures 5A, 5B:
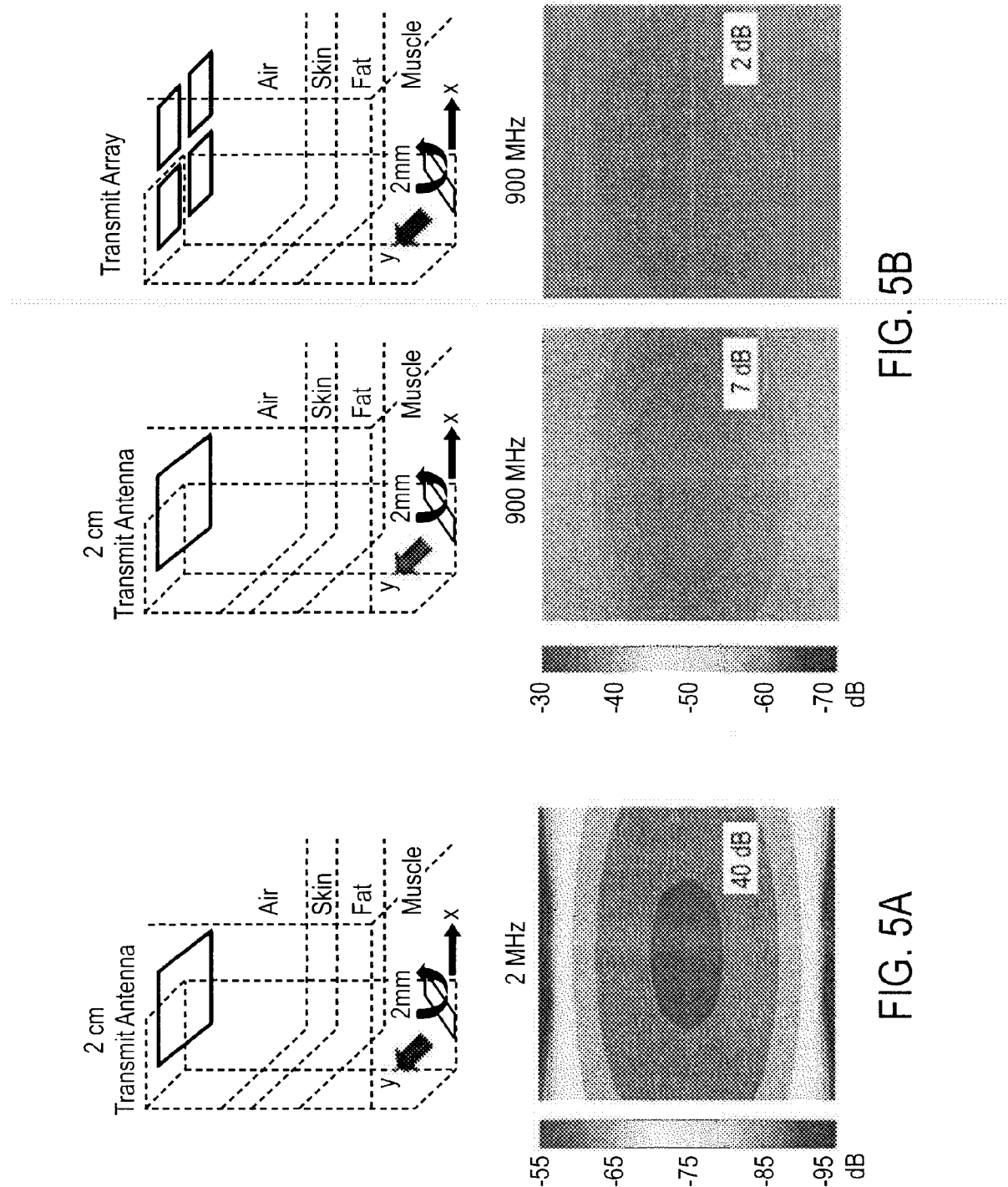
FIGS. 5a-5b illustrate variations and differences in the power transfer efficiency.

This example considers the variation of the power transfer efficiency due to displacement and orientation of the receive coil. Referred to FIG. 5, the receive coil is moved along the x-axis and the y-axis, and it is tilted by 0 to 60°. At transmission frequency of 2 MHz, FIG. 5A shows the variation of the power transfer efficiency at different receiver location. The differences in the power transfer efficiency can be 40 dB. At transmission frequency of 900 MHz, FIG. 5B shows that the differences in the power transfer efficiency are about 7 dB. Furthermore, when multiple antennas are used at the external transceiver, the differences in the power transfer efficiency are less than 2 dB. Therefore, the present invention is relatively insensitive to the displacement and orientation of the receive antenna on the internal transceiver.

FIG. 6 shows advantages of using radiating near field according to the present invention as contrasted to near field and far field.

Figure 7:
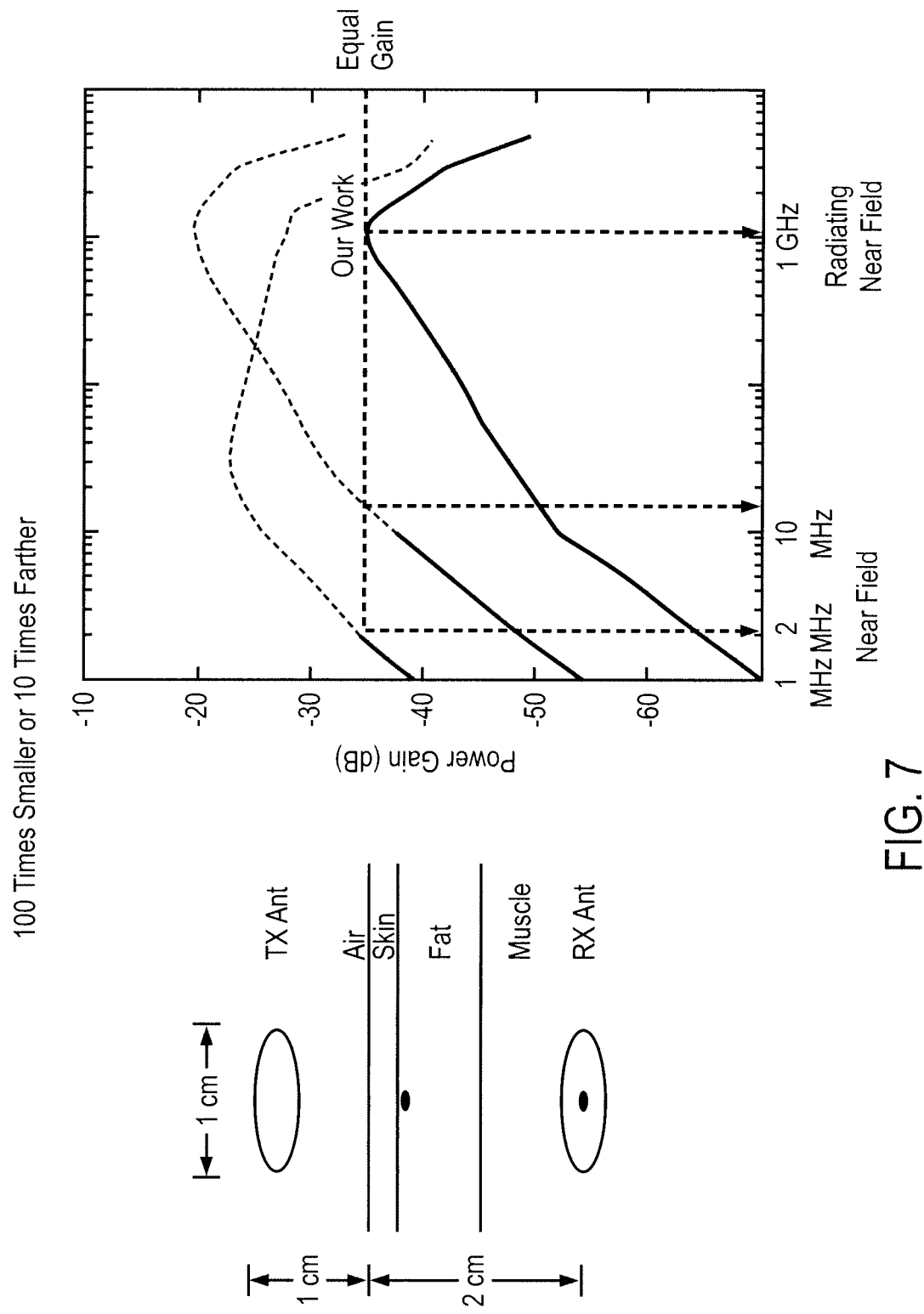
FIG. 7 shows how the present invention can result in a device that is 100 times smaller than conventional devices or one that can transfer 10 times farther.

FIG. 7 shows how the present invention can result in a device that is 100 times smaller than conventional devices or one that can transfer 10 times farther.

Figure 8:
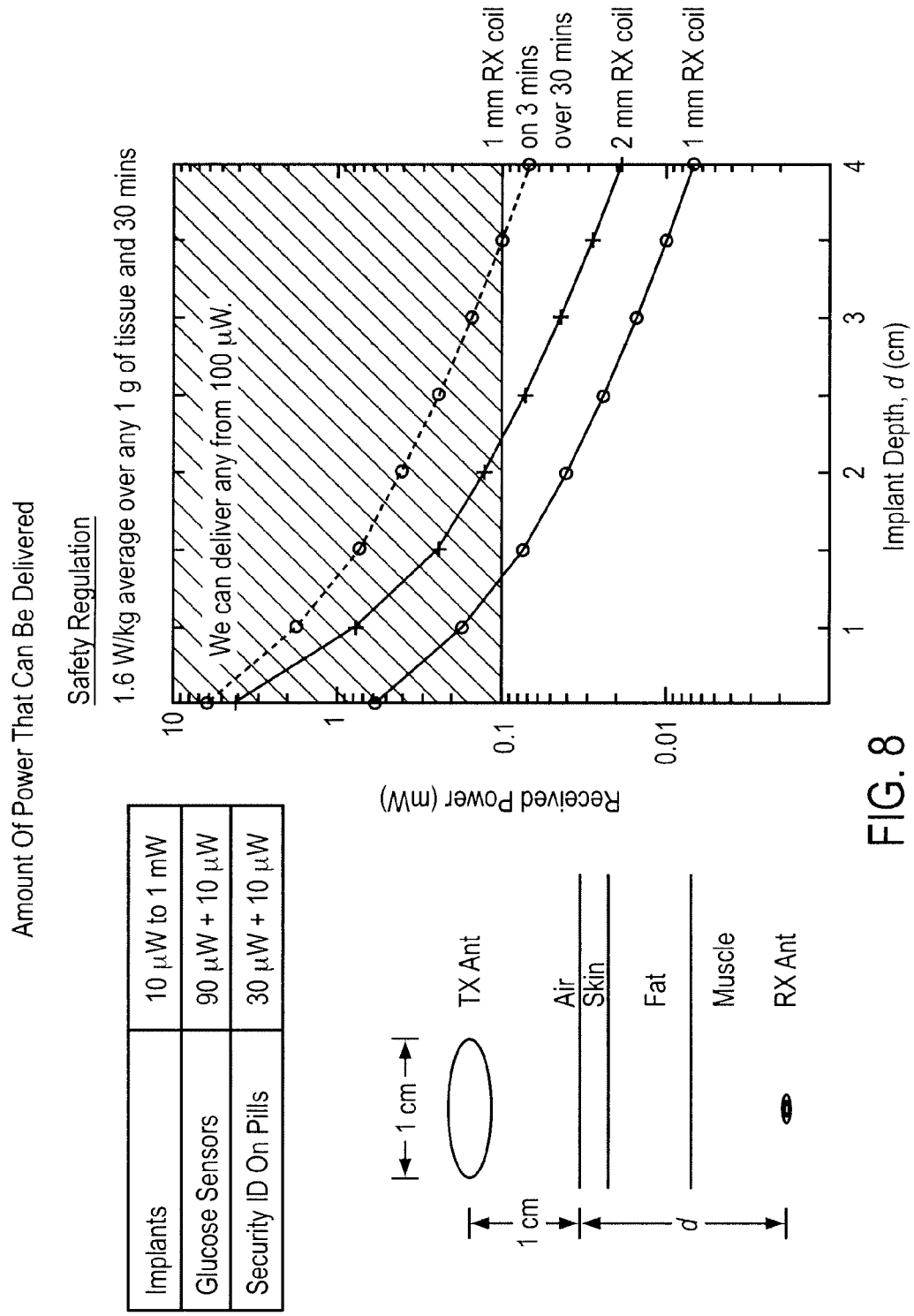
FIG. 8 shows ranges of power that can be transferred according to implant depth.

FIG. 8 shows ranges of power that can be transferred according to implant depth.

Further Considerations

Adaptive Matching and Rectification

As discussed above a specific use for the wireless power transfer described herein is an implanted neural sensor whose clinical requirements constrain the implanted receiver size to 2 mm×2 mm and specify an implant depth of 15 mm. Ranges in the size of the receive antenna within this device are thus less than 2 mm×2 mm. It is noted, however, that while the apparatus and techniques herein are most useful when the size of one or both antennae is less than or equal to about 10 times the distance between the antennae, that other applications may well exist.

The wireless power link described herein achieves equivalent link gain as conventional inductively coupled links but uses a 100 times smaller receive antennae, enabling mm-sized implanted devices. This development requires three steps: first, determine the optimal frequency for wireless power transfer through tissue to area constrained receive antennae. Second, recognize that to achieve the theoretical maximum gain we must employ a simultaneous conjugate match and make that match robust to inevitable range and dielectric variations associated with a medical implant. And third, develop a highly efficient low voltage rectifier. Each of these are discussed hereinafter I. Optimal Frequency A. Optimality Criteria In order to determine the optimal frequency for wireless power transfer through tissue optimality criteria must be chosen. There are two potential candidates: for a given power delivered to the implanted device are we most concerned with minimizing losses in the tissue or with minimizing transmit power. This can be expressed quantitatively as: do we seek to maximize (i) link efficiency, $\eta_{link}$, given by the ratio of average power received by the load, $P_{rec}$, average power loss in the tissue, $P_{tissue,loss}$, or (ii) link gain, $G_{link}$, given by the ratio of average power received by the load, $P_{rec}$, to average power input to the transmitter, $P_{in}$.

$$\eta_{link} = \frac{P_{rec}}{P_{tissue,loss}} \quad (1)$$

$$G_{link} = \frac{P_{rec}}{P_{in}} \quad (2)$$

Minimizing tissue losses and thus tissue heating is a critical specification whereas complexity and power consumption at the transmitter are lower priorities. Therefore we define $f_{opt}$ as the transmission frequency which maximizes $\eta_{link}$. This guides our analytical derivation of $f_{opt}$. However $\eta_{link}$ is difficult to measure experimentally whilst measurement of $G_{link}$ is straightforward. Fortunately, as will be shown, we can use $G_{link}$, subject to certain constraints, to demonstrate $f_{opt}$ experimentally.

B. Analytical Solution

Tissue permittivity is a complex function of frequency and can be expressed using the debye relaxation model, shown in Eq. (3), where τ is the dielectric relaxation constant, $\epsilon_{r0}$ is the relative permittivity at frequencies ω<<1/τ, $\epsilon_\infty$ is the relative permittivity at ω<<1/τ, $\epsilon_\infty$, and σ is the dc conductivity.

$$\epsilon_r(\omega) = \epsilon_\infty + \frac{\epsilon_{r0} - \epsilon_\infty}{1 - i\omega\tau} + i\frac{\sigma}{\omega\epsilon_0} \quad (3)$$

The imaginary component of $\epsilon_r(\omega)$ includes the static conductivity σ and so dielectric loss in this model includes both relaxation loss and induced-current loss. The model is valid from the frequency at which $\in_{r0}$ is measured to frequencies much less than $1/\tau$. For example, the parameters for muscle tissue are: $\tau=7.23$ ps, $\in\infty=4$, and $\in_{r0}=54$ and the model is valid for frequencies f such that 2.8 MHz $<<f>>$ 140 GHz.

Including this model for permittivity in the full-wave electromagnetic analysis of the link we can derive the link efficiency and link gain as a function of frequency. The maximum efficiency for wireless power transmission from a transmitter, modeled by a magnetic current density, in free space to an area constrained receiver, modeled by a magnetic dipole of area $A_r$, in tissue dielectric and loaded by impedance $Z_L$ is given approximately in Eq. (4).

$$\eta_{link} \approx \tag{4}$$

$$\frac{3k_{I0}e^{-2k_{I0}d}A_r^2\mathrm{real}\left(\frac{1}{Z_L}\right)}{2\pi\sigma d^4}\left[\left(\frac{d^2\epsilon_{r0}}{c^2} + \frac{d\tau(\epsilon_{r0} - \epsilon_\infty)}{c\sqrt{\epsilon_{r0}}}\right)(|\beta_{-1}|^2 + |\beta_1|^2)\omega^2 + \right.$$

$$\left. 4|\beta_0|^2 - |\beta_{-1}|^2 - |\beta_1|^2 + 2k_{I0}d(|\beta_{-1}|^2 + |\beta_1|^2)\right]e^{-\frac{d\tau(\epsilon_{r0}-\epsilon_\infty)}{c\sqrt{\epsilon_{r0}}}\omega^2}$$

where $$k_{I0} = \frac{\sigma}{2}\sqrt{\frac{\mu 0}{\epsilon 0\epsilon - 0}}, d$$

is implant depth, the center of the receiver is on the axis normal to the transit current density plane and $\beta_{-1}$, $\beta_0$ and $\beta_1$ are the components of the unit vector describing the orientation of the receiver relative to the axis of the transmitter. The maximum efficiency is achieved at frequency $$\omega_{opt}^2 = \frac{c\sqrt{\epsilon_{r0}}}{d\tau(\epsilon_{r0} - \epsilon_\infty)}\frac{4|\beta_0|^2 - |\beta_{-1}|^2 - |\beta_1|^2 + 2k_{I0}d(|\beta_{-1}|^2 + |\beta_1|^2)}{\left(\frac{d^2\epsilon_{r0}}{c^2} + \frac{d\tau(\epsilon_{r0} - \epsilon_\infty)}{c\sqrt{\epsilon_{r0}}}\right)(|\beta_{-1}|^2 + |\beta_1|^2)} \tag{5}$$

In general, $\frac{d^2\epsilon_{r0}}{c^2} \gg \frac{d\tau(\epsilon_{r0} - \epsilon_\infty)}{c\sqrt{\epsilon_{r0}}}$. $\tag{6}$ Therefore, we have $\omega_{opt} \approx \sqrt{\frac{c\sqrt{\epsilon_{r0}}}{d\tau(\epsilon_{r0} - \epsilon_\infty)}}$ The optimal frequency is approximately inversely proportional to the square root of implant depth and to the dielectric relaxation constant.

The dielectric properties of many biological tissues types have been characterized by others, as shown in the Table below. The parameters for the 4-term Cole-Cole model which is a variant of the Debye relaxation model. Conversion to the Debye relaxation model is as follows:

$$\tau = \tau_1, \epsilon_{r0} = (\epsilon_{r0} - \epsilon_\infty), \text{ and } \sigma = \sum_{n=2}^{4}\frac{\epsilon_0(\epsilon_{r0}-\epsilon_\infty)}{\tau_n} + \sigma_s$$

TABLE I

APPROXIMATE OPTIMAL FREQUENCY FOR TEN DIFFERENT TYPES OF BIOLOGICAL TISSUE, ASSUMING d = 1 CM

| Tissue Type | Approximately $f_{opt}$ (GHz) |
|---|---|
| Blood | 3.54 |
| Bone (cancellous) | 3.80 |
| Bone (cortical) | 4.50 |
| Bone (grey matter) | 3.85 |
| Brain (white matter) | 4.23 |
| Fat (infiltrated) | 6.00 |
| Fat (not infiltrated) | 8.64 |
| Muscle | 3.93 |
| Skin (dry) | 4.44 |
| Skin (wet) | 4.01 |
| Tendon | 3.17 |

That data is used to calculate the approximate optimal frequencies for ten different kinds of tissue assuming d=1 cm, as listed in Table I. All approximate optimal frequencies are in the GHz-range. The optimal frequency decreases as the transmit-receive separation increases but remains above 1 GHz even up to d=10 cm. This suggests that for any potential depth of implant inside the body, the asymptotic optimal frequency is around the GHz-range for small transmit and small receive sources.

C. Empirical Validation $\eta$link is difficult to measure experimentally whilst measurement of Glink is straightforward. Here it is shown that the maxima of $\eta$link and Glink occur at the same frequency for small antenna sizes although they diverge significantly as antenna size increases. Therefore the optimal frequency can be validated experimentally for small antennae by measuring Clink versus frequency.

Energy conservation says that average power into the transmit antenna is equal to average power out of the receive antenna plus the average power dissipated in the link as expressed in Eq. (7).

$$P_{in} = P_{rec} + P_{loss,total} \tag{7}$$

where total power dissipation in the link, $P_{loss,total}$, takes three forms: resistive losses in the antennae, $P_{wire,loss}$; loss in the tissue, $P_{tissue,loss}$; and radiation loss, $P_{rad,loss}$.

$$P_{loss,total} = P_{tissue,loss} + P_{rad,loss} + P_{wire,loss} \tag{8}$$

Dividing across Eq. (7) by $P_{rec}$ gives $$\frac{1}{G_{link}} = 1 + \frac{P_{loss,total}}{P_{rec}} \tag{9}$$

A wavelength in a lossy dielectric medium is given by $$\lambda = \frac{2\pi}{\mathrm{Im}(\gamma)} \tag{10}$$

where $\gamma$ is the propagation constant given by $$\gamma = \sqrt{j\omega\mu(\sigma + j\omega\in)} = \omega\sqrt{-\mu\in_{eff}} \tag{11}$$

and effective permittivity, $$\epsilon_{eff} = \epsilon - j\frac{\sigma}{\omega}.$$

The permittivity of muscle at 1 GHz is given by $C_{eff}$= (54.811–17.582j) $C_0$ and so $\lambda_{muscle, 1GHz}$=4 cm. For electrically small, i.e. circumference≤$\lambda$/5, square loop antennae the radiated power can be modelled by a resistance $R_{rad}$ in series with the antenna:

$$R_{rad} = \frac{4}{3} \text{Re}\left(\sqrt{\frac{\mu}{\epsilon_{eff}}}\right) \pi^3 \left(\frac{NA}{\lambda^2}\right)^2 \quad (12)$$

where N is the number of turns in the loop and A is the area of the loop. For the experiment 2 mm×2 mm square loop antennae were used at the transmitter and receiver. The radiation resistance of a 2 mm×2 mm square loop antenna driven at 1 GHz in free space is $R_{rad,free\,space}$=30.8 µΩ. Whilst the radiation resistance of the same antenna, at the same frequency in muscle dielectric is $R_{rad,muscle}$=12.5 mΩ. For a 2 mm×2 mm square loop antenna driven at 1 GHz with free space on one side and muscle tissue on the other we expect the radiation resistance to be between these two values, and certainly we can take $R_{rad,muscle}$=12.5 mΩ as an upper bound.

The antennae were realized using 200 µm wide 1-oz copper metallization traces on a PCB. 1-oz copper has a thickness of t=1.3 mil=33 µm. The conductivity of copper is $\sigma_{Cu}$=60×10$^6$ Sm$^{-1}$ so that at 1 GHz the skin depth is $\delta$Cu=2 µm. Thus the metallization thickness is much greater than a skin depth. The current will stay on one face of a planar loop above a lossy dielectric and so the series resistance of the loop is given by $$R_{series\,loop} \approx \frac{l}{\omega\sigma\delta\left(1 - e^{-\frac{t}{\delta}}\right)} \quad (13)$$

The antenna loop and feedlines are l=2.18 mm long. Thus at 1 GHz the series resistance is $$R_{wire,\,1\,GHz} \approx 0.09\Omega \quad (14)$$

The link consisting of two 2 mm×2 mm square loop antenna separated by 15 mm of tissue was simulated using a 3D electromagnetic solver and the s-parameters of the two-port were found. At the frequency of interest those s-parameters can be transformed to a lumped equivalent circuit, valid only at that frequency, by transforming the 2×2 s-parameter matrix, S, to a 2×2 z-parameter matrix, Z, as in Eq. (15).

$$Z = \begin{bmatrix} Z_{11} & Z_{12} \\ Z_{21} & Z_{22} \end{bmatrix} = Z_0(I - S)^{-1}(I + S) \quad (15)$$

where $Z_0$ is the characteristic impedance assumed in measuring the S-parameters. $Z_{12}=Z_{21}$ and thus the link can be represented using a lumped T-model at each frequency, which will be useful later. The coupling is quite weak, the maximum achievable gain being −41 dB, and so losses due to the transmit loop current are much greater than losses due to the much smaller receive loop current. Losses due to the transmit loop current are given by $$P_{loss,total} \approx |I_{Tr\,Loop}|^2 Re(Z_{11}) \quad (16)$$

Substituting this into Eq. (8) we have $$|I_{Tr\,Loop}|^2 Re(Z_{11}) \leq |I_{Tr\,Loop}|^2 (R_{tissue}+R_{rad}+R_{wire}) \quad (17)$$

$$\Rightarrow R_{tissue} \geq Re(Z_{11})-(R_{rad}+R_{wire}) \quad (18)$$

Simulation gives $Re(Z_{11})$=0.4224Ω and we have $R_{rad}$<0.0125Ω and $R_{wire}$=0.09Ω so clearly $$R_{tissue} >> R_{rad}+R_{wire} \quad (19)$$

$$\Rightarrow \frac{P_{rec}}{P_{loss,total}} \approx \frac{P_{rec}}{P_{tissue,loss}} = \eta_{link} \quad (20)$$

Substituting Eq. (20) into Eq. 9) gives $$\frac{1}{G_{link}} \approx 1 + \frac{1}{\eta_{link}} \quad (21)$$

which gives the following correspondences between $G_{link}$ and $\eta_{link}$ $$G_{link} = \frac{\eta_{link}}{1 + \eta_{link}} \quad (22a)$$

$$\eta_{link} = \frac{G_{link}}{1 - G_{link}} \quad (22b)$$

The link is a passive system and so $0<P_{rec}<$Pfb or equivalently $0<G_{Link}<1$. As can be seen from Eqs. (22) $G_{link}$ is a monotonically increasing function of $\eta_{link}$ for the range $0<G_{link}<1$ and $\eta_{link}$ is a monotonically increasing function of $G_{link}$ for the domain $0<G_{link}<1$. Therefore maximizing $G_{link}$ is equivalent to maximizing $\eta_{link}$ and vice versa. Correspondingly maximum link gain and maximum link efficiency occur at the same transmission frequency for 2 mm×2 mm square loop antennae separated by 15 mm of tissue. For 20 mm×20 mm square loop antennae the radiation loss becomes much more significant and the maximum value of $G_{link}$ occurs at a significantly lower frequency than the maximum value of $\eta_{link}$.

Experiments were run using 15 mm of bovine muscle tissue between the two antennae. Muscle dielectric was also placed behind the RX antenna, which is omitted from the diagram for clarity. The antennae were aligned axially. Nylon braces through on board vias were used to ensure accurate antenna alignment without disturbing the field. If the antennae were fed by SMA-PCB jacks close to the antennae then the link gain would be dominated by coupling between the connectors rather than antennae coupling as the connector size is large relative to the antennae and range. To ensure the measured coupling is that between the antennae only, the antennae are fed using 50Ω stripline, which provides shielding on both sides of the signal line, and a 320 µm thick dielectric between signal line and each ground plane is used to ensure that separation between signal and ground of the feedline is small compared to the antenna size and range. In order to measure $G_{link}$ directly we would need to simultaneously conjugate match the link to the source and load impedances as will be discussed short. We wish to measure $G_{link}$ over a broad range of frequencies, and it would not be feasible to develop a match for each of these frequency points. Instead the s-parameters of the link were measured using a network analyzer and de-embedded to the plane at the input to the transmit antenna and the plane at the output of the receive antenna. Using these de-embedded s-parameters the maximum achievable gain was calculated according to Eq. (23).

$$G_{mo} = \frac{|S_{21}|}{|S_{12}|}(k - \sqrt{k^2 - 1}) \quad (23)$$

where the stability factor, k, is defined in terms of the link's s-parameter representation as in Eq. (24)

$$k = \frac{1 - |S_{11}|^2 - |S_{22}|^2 + |D|^2}{2|S_{12}||S_{21}|} \quad (24)$$

and $$D = S_{11}S_{22} - S_{12}S_{21} \quad (25)$$

Usually |D|<1 in which case k>1 is sufficient to guarantee unconditional stability. The link is purely passive and thus unconditionally stable.

Figure 9:
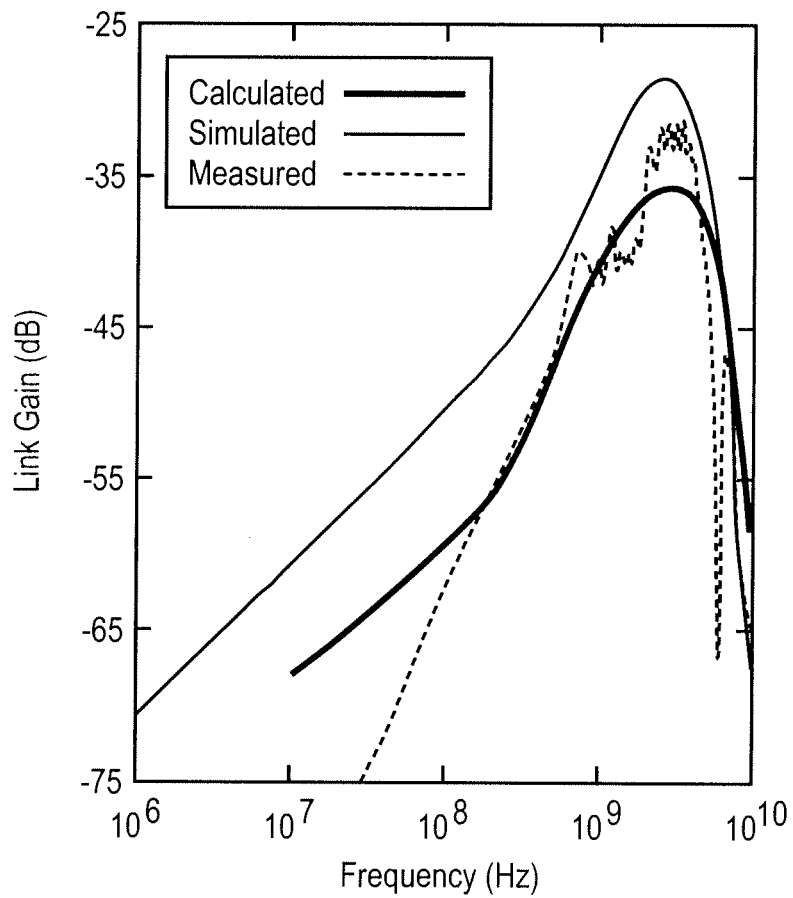
FIG. 9 shows different gain versus frequency plots.

The gain was also simulated using both finite element and method of moments based 3D electromagnetic solvers. It was found that the method of moments based solver, Agilent's Momentum in full wave mode, gave the fastest convergence and results which most closely matched experiment for the antenna sizes and range of interest. The measured, simulated and calculated link gains are plotted versus frequency in FIG. 9 for an implant depth of 15 mm, using 2 mm×2 mm loop antennae. Very similar shapes and similar optimum frequency of $f_{opt} \approx 3$ GHz are seen for all three. Beyond this frequency the tissue polarization cannot keep up with the applied electric field. The phase delay between the electric field and the polarization incurs very high energy loss, killing the gain quickly. This plot is for muscle tissue only. When layered media are considered, modeling anatomy by layers of skin, fat, muscle etc., $f_{opt}$ falls due to increased radiation losses caused by greater impedance mismatches between the layers at higher frequency. Since the transmitter size is less constrained the implemented link consists of a 2 cm×2 cm transmit antenna, a 2 mm×2 mm receive antenna. Simulation with these antenna sizes and a layered tissue model give an optimum frequency just below 1 GHz. Therefore the link was designed to operate at 1 GHz and at ISM band frequency 915 MHz.

II. Matching Technique

A. Field Region

To understand which circuit techniques should be used to interface to the antennae we must first determine the field type. Near field is defined as when the range is much less than a wavelength, d<<λ. In this case the link is essentially just a transformer. Quasi-static analysis is sufficient and loaded resonant tuning achieves the maximum link gain. The far field is defined as when the range is much greater than a wavelength, d<<λ. This is the case in most wireless communications links, in which interaction between the antenna is negligible and one matches to the antenna impedance and the impedance of the medium. At 1 GHz a wavelength in tissue, $\lambda_{tissue}$, is about 4 cm depending on the tissue composition. The range in tissue, d=1.5 cm, is of the same order of magnitude as $\lambda_{tissue}$. Therefore neither near field nor far field approximations can be applied. Consequently neither resonant tuning nor matching to the impedance of the antenna and medium achieve maximum link gain. Resonant tuning comes closer and we will compare that to our solution. First we consider the type of resonant tuning to be used.

B. Resonant Tuning

Figure 10:
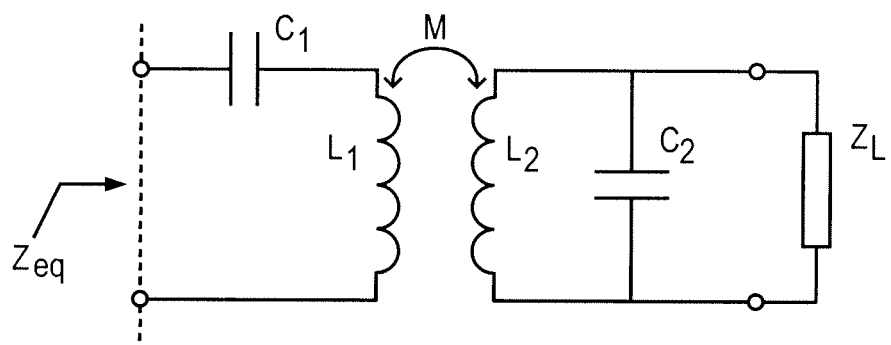
FIG. 10 shows an embodiment of series tuning of the transmitter and shunt tuning of the load.

Many publications have described the use of inductive links to power implanted devices and many different techniques have been proposed for tuning depending on whether the source is a current or voltage source, whether the tuning is in shunt or series and whether loading effects are considered. Others have shown that series tuning of the transmitter and shunt tuning of the load, as illustrated in FIG. 10, is most appropriate when the source is most closely approximated by a voltage source. The two most popular methods of tuning are unloaded tuning and free-running oscillation a.k.a. loaded tuning. For unloaded tuning the tuning capacitances of FIG. 10 are chosen according to $L_1C_1 =$ $$L_2C_2 = \frac{1}{\omega^2}$$

where $L_1$ and $L_2$ are the inductances of the transmit and receive coils respectively. The requirements for loaded tuning are given by Eq. (26)

$$L_1C_1 = \frac{1}{\omega^2} \quad (26a)$$

$$X_2 = \omega L_2 - \frac{\omega C_2 R_L^2}{1 + \omega^2 C_2^2 R_L^2} = 0 \quad (26b)$$

where $X_2$ is the reactive part of secondary inductance $L_2$ in series with the parallel combination of $C_2$ and $R_L$. Together Eqs. (26) ensure that the impedance seen looking into the resonant link, $Z_{eq}$ in FIG. 10, is purely real and that the impedance seen looking from the mutual inductance in both directions is purely real, provided the source impedance has no reactive component.

Solving gives the design equations:

$$C_1 = \frac{1}{\omega^2 L_1}$$

for both loaded and unloaded tuning, $$C_2 = \frac{1}{\omega^2 L_1}$$

for unloaded shunt tuning and $$C_2 = \frac{R_L \pm \sqrt{R_L^2 - 4\omega^2 L_2^2}}{2\omega^2 R_L L_2} \quad (27)$$

for loaded tuning where $R_L$ is the load resistance. A solution for $C_2$ in the loaded resonant tuning case exists if and only if $R_L > 2\omega L_2$. The 2 mm×2 mm square loop antenna of the implanted receiver has an inductance of $L_2$=4.64 nH which means that at f=1 GHz a solution exists when $R_L$>58Ω. We are interested in much higher load impedances and so a solution will exist. When $R_L >> \omega L_2$, which is true for our link, then Eq. (27) reduces to $$C_2 = \frac{1}{\omega^2 L_1}$$

and so loaded tuning and unloaded tuning are equivalent for this link.

C. Simultaneous Conjugate Matching

The link has two ports and is linear. The link is purely passive and thus unconditionally stable. A well-known result in microwave and RF circuits is that, for a given source impedance, simultaneous conjugate matching of a stable linear two-port to the source and load impedances achieves the maximum power gain from the source to the load. The maximum achievable power gain is given in terms of the s-parameters of the link as $G_{ma}$ in Eq. (23), and is independent of the load impedance. This is a standard technique to maximize amplifier power gain, but has not previously been used in wireless power transfer links.

To realize the simultaneous conjugate match we need matching networks which produce reflection coefficients, $\Gamma_{Sm}$ and where D is specified in Eq. (25).

TABLE II

EXISTENCE CONDITIONS FOR L-MATCHES

| Existence Conditions | L-section types |
| --- | --- |
| $R_{S_m} > R_S \cdot |X_S| \geq \sqrt{R_S(R_{S_m} - R_S)}$ | Normal and Reversed |
| $R_{S_m} > R_S \cdot |X_S| < \sqrt{R_S(R_{S_m} - R_S)}$ | Normal Only |
| $R_{S_m} < R_S \cdot |X_{S_m}| \geq \sqrt{R_{S_m}(R_S - R_{S_m})}$ | Normal and Reversed |
| $R_{S_m} < R_S \cdot |X_{S_m}| < \sqrt{R_{S_m}(R_S - R_{S_m})}$ | Reversed Only |

Figure 11:
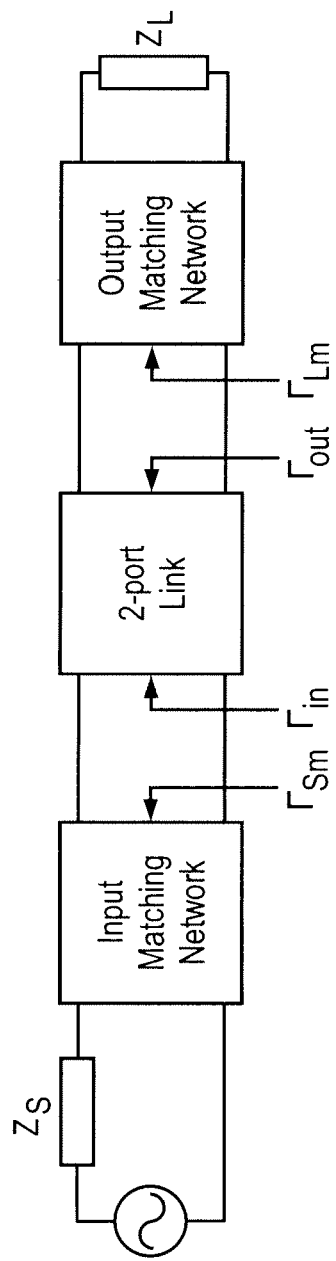
FIG. 11 illustrates a matching network according to an embodiment.

$\Gamma_{Lm}$, specified in Eq. (28) and Eq. (29)

$$\Gamma_{Sm} = \frac{C_1^\dagger}{|C_1|}\left[\frac{B_1}{2|C_1|} - \sqrt{\frac{B_1^2}{|2C_1|^2} - 1}\right] \tag{28}$$

$$\Gamma_{Lm} = \frac{C_2^\dagger}{|C_2|}\left[\frac{B_2}{2|C_2|} - \sqrt{\frac{B_2^2}{|2C_2|^2} - 1}\right] \tag{29}$$

where $$B_1 = 1 - |S_{22}|^2 + |S_{11}|^2 - |D|^2 \tag{30}$$

$$C_1 = S_{11} - DS_{22}^\dagger \tag{31}$$

$$B_2 = 1 - |S_{11}|^2 + |S_{22}|^2 - |D|^2 \tag{32}$$

$$C_2 = S_{22} - DS_{11}^\dagger \tag{33}$$

and where D is specified in Eq. 25. It is noted that the $\Gamma'_{Lm}$ as specified in Equations 28 and 29 is also illustrated in FIG. 11.

The power link is a narrowband system and so two-element L-matching sections are sufficient. Calculation of the component values for a lumped L-match is straight forward and described in texts. A brief outline of these calculations is given here for the source match, transforming $Z_S$ to $Z_{S_m}$. The load match, transforming $Z_L$, to $ZL_m$, can be calculated similarly. First we convert the required refection coefficient to an impedance $$Z_{S_m} = R_{S_m} + jX_{S_m} = Z_0\left(\frac{1+\Gamma_{Sm}}{1-\Gamma_{Sm}}\right) \tag{34}$$

where $Z_0$ is the reference impedance used in measuring the S-parameters.

Figure 12:
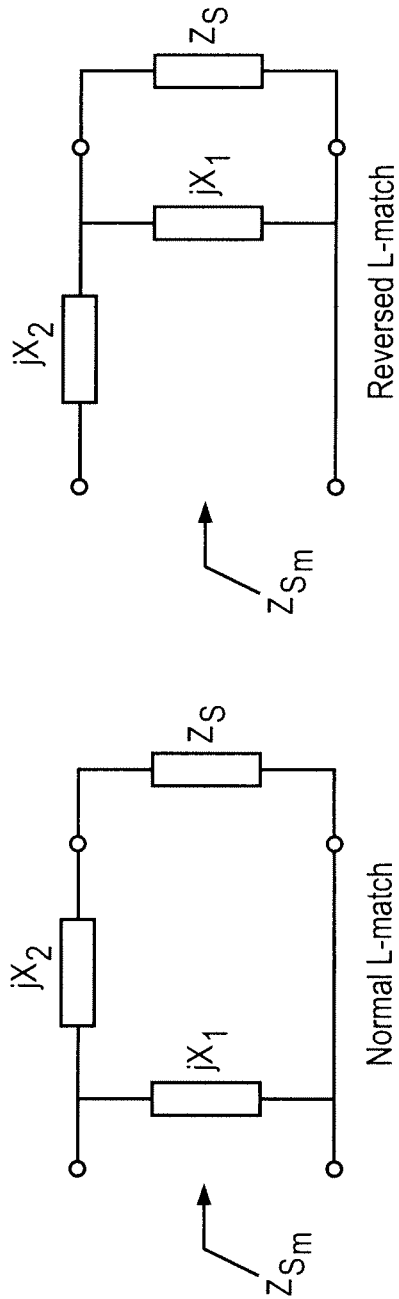
FIG. 12 shows Normal type L-match component reactances and reversed type L-match component reactances.

There are two types of L-match which can be used to transform an impedance $Z_S$ to another $Z_{S_m}$ as illustrated in FIG. 12. Which type of L-match exists is determined using Table II, in which $ZS = R_S + jX_S$ and $Z_{S_m} = R_{S_m} + jX_{S_m}$. Normal type L-match component reactances are given by Eq. 35 and reversed type L-match component reactances by Eq. 36 according to the naming convention illustrated in FIG. 12.

$$X_1 = \frac{-X_{S_m} \pm R_{S_m}Q}{\frac{R_{S_m}}{R_S} - 1} \tag{35a}$$

$$X_2 = -(X_S \pm R_S Q) \tag{35b}$$

$$Q = \sqrt{\frac{R_{S_m}}{R_S} + \frac{X_{S_m}^2}{R_{S_m}R_S} - 1} \tag{35c}$$

$$X_1 = \frac{-X_S \pm R_S Q}{\frac{R_S}{R_{S_m}} - 1} \tag{36a}$$

$$X_2 = -(X_{S_m} \pm R_{S_m}Q) \tag{36b}$$

$$Q = \sqrt{\frac{R_S}{R_{S_m}} + \frac{X_S^2}{R_{S_m}R_S} - 1} \tag{36c}$$

D. Comparison of Resonant Tuning and Simultaneous Conjugate Matching

Link gains under both resonant tuning and simultaneous conjugate matching are compared for two links. Link 1, is the link we used to verify the optimal frequency and consists of 2 mm×2 mm square loop antennae at both the transmit and receive sides with the transmitter placed 1 mm above the tissue and the receiver placed 15 mm deep into the tissue with source and load impedances of 50Ω. Link 2 is the implemented system. The transmit antenna size is less constrained as it is outside the body so we use a 2 cm×2 cm square loop transmit antenna and a 2 cm×2 cm square loop receive antenna placed 15 mm deep into the tissue. The transmit loop is placed 1 cm above the tissue to allow practical packaging thickness and to ensure that SAR regulations are met. The source impedance is 50Ω and load impedance is 13.9 kΩ∥28.7 fF which represents the loaded rectifier as will be explained later. In both cases the antennae are axially aligned and their axis is perpendicular to the tissue surface.

1) Link 1: The inductance of the antenna and its feed-lines was estimated using Agilent ADS Momentum giving L=4.64 nH for the 2 mm×2 mm loop and so $$C_1 = C_2 = \frac{1}{\omega^2 \times 4.64 \text{ nH}} = 5.46 \text{ pF}$$

are required at 1 GHz. Simulation of the resonant tuned link gives $G_{Link\ 1} = -52.2$ dB.

The s-parameters of the simulated link 20 mm×20 mm 20 mm Tx and 2 mm×2 mm Rx separated by 1 mm of free space and 15 mm of tissue were calculated using also Momentum.

$$S = \begin{bmatrix} -0.494 + j0.855 & (1.577 + j1.454) \times 10^{-4} \\ (1.577 + j1.454) \times 10^{-4} & -0.490 + j0.855 \end{bmatrix} \tag{37}$$

These s-parameters were used to calculate the simultaneous conjugate match. A lumped T-network was calculated by transforming the s-parameters to impedance parameters using Eq. (15). Circuit simulation of this link model and simultaneous conjugate match gives $G_{Link\ 1} = 41.9$ dB.

TABLE III

COMPARISON OF LINK GAINS UNDER RESONANT TUNING AND SIMULTANEOUS CONJUGATE MATCHING

|  | Link 1 | Link 2 |
| --- | --- | --- |
| Gain with Resonant Tuning (dB) | −52.2 | −46.3 |
| Gain with Sim Conj Match (dB) | −41.9 | −32.5 |

2) Link 2: Momentum gives an inductance of L=47.6 nH for the 20 mm×20 mm loop. Our load is 13.9 kΩ∥128.7 fF at 1 GHz, so for resonant tuning we assume $Z_L$=13.9 kΩ and subtract 28.7 fF from the calculated value for $C_2$. For 20 mm×20 mm Tx and 2 mm×2 mm Rx we calculate $$C_1 = \frac{1}{\omega^2 \times 47.6 \text{ nH}} = 0.532 \text{ pF}$$

And $$C_2 = \frac{1}{\omega^2 \times 4.64 \text{ nH}} = 5.46 \text{ pF}$$

at 1 GHz. Simulation of the resonant tuned link gives $G_{Link\ 2}$=−46.3 dB.

The s-parameters of the simulated link (2 cm tx, 10 mm free space, 15 mm tissue, 2 mm rx) are:

$$S = \begin{bmatrix} 0.9610 + j0.2384 & (0.6169 - j7.124) \times 10^{-4} \\ (0.6169 - j7.124) \times 10^{-4} & -0.4374 + j0.8726 \end{bmatrix} \quad (38)$$

Figure 13:
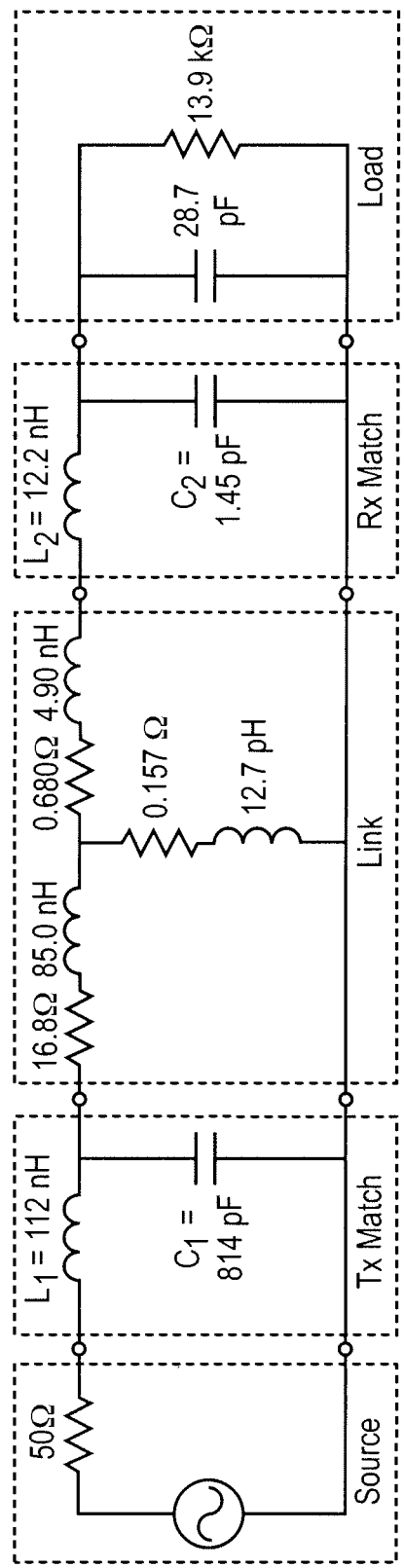
FIG. 13 illustrates an embodiment of the link model and simultaneous conjugate matches.

Again we can transform these s-parameters to a lumped T-model valid at that frequency. The link model and simultaneous conjugate matches are illustrated in FIG. 13. Simulation of the link with simultaneous conjugate matching $G_{Link\ 2}$=−32.5 dB.

For both links simultaneous conjugate matching results in more than 10 dB higher link gain than resonant tuning as summarized in Table III.

E. Match Sensitivity

The simultaneously conjugate matched link will allow maximum power transfer from the source to the load provided the link is modeled correctly and the match component values are accurate. However link parameters cannot be known accurately prior to deployment due to variation in implant depth; misalignment between antennas; and variation in tissue composition between subjects (e.g. different fat/muscle ratios). Hence the required match components cannot be known exactly.

Figure 14:
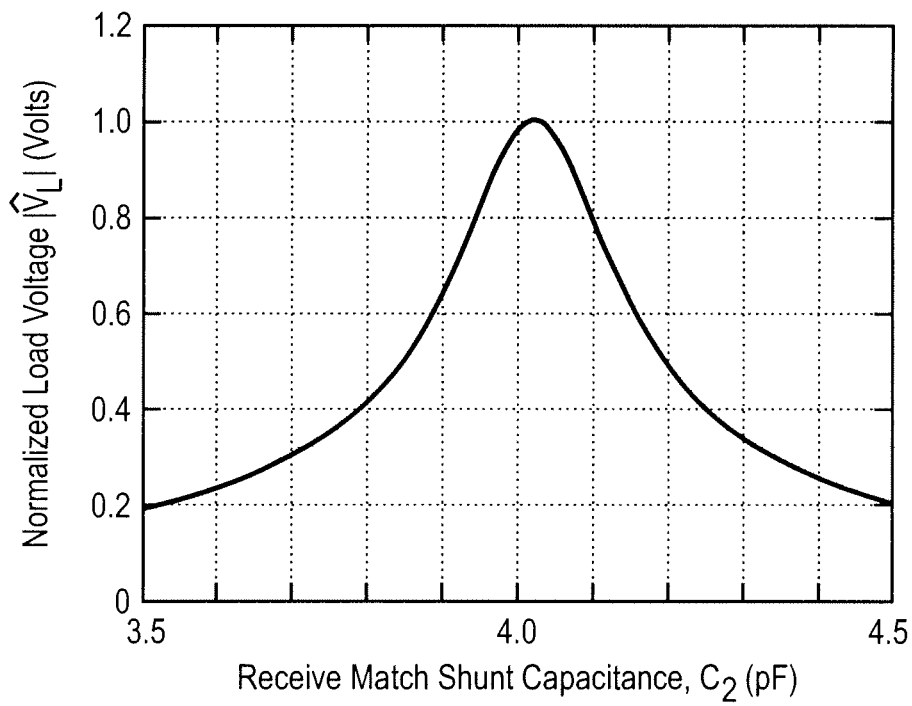
FIGS. 14 and 15 show graphs of receive match shunt capacitance to normalized load voltage and gradient of load voltage, respectively.

To analyse the sensitivity of link gain to placement accuracy and tissue thickness we consider a ±1 mm placement inaccuracy. The s-parameters of the link with 15 mm implant depth and perfect alignment between the Tx and Rx antenna were measured and the receive side match components were calculated as a series inductance L2=1.05 nH and a shunt capacitance $C_2$=4.02 pF. The measured s-parameters were transformed to a lumped T-model which was simulated with the calculated match component values. The simulated link-gain equalled the theoretical maximum achievable gain for the ideal link $G_{ma,Link_{ideal}}$=28.4 dB. The s-parameters of a second link wherein the implant depth is increased by 1 mm and the antennae are misaligned by 1 mm were measured. The receive side matching components were calculated as $L_2$=1.55 nH and $C_2$=4.08 pF. Simulation of this link with its match component values shows that link gain equals the maximum achievable gain $G_{ma,Link_{actual}}$=28.6 dB. However if the match components for the ideally aligned link were used with this marginally misaligned link, the link gain would be −31.8 dB, a decrease of 3.2 dB for only ±1 mm placement inaccuracy. More generally, FIG. 14 shows the variation of $|V_L|$ the normalized magnitude of the voltage across the load, with the receive match shunt capacitance, $C_2$. It can be seen $|V_L|$ has a maximum at the design value of $C_2$=4.02 pF and falls off sharply as $C_2$ varies. In fact if $C_2$ is only 2.5% different from the design value, i.e. $C_2$=3.91 pF, $|V_L|$ falls by 66%. Therefore it is critical that a precise $C_2$ be used.

F. Adaptive Matching

Since the precise match component values cannot be known at the design phase and the link gain is so sensitive to those parameters it is needed to autonomously adapt the match to compensate for tissue and placement variations and thus ensure maximum power transfer to the load.

If the performance surface is parabolic or similar to parabolic in the region of interest then gradient search can be used. FIG. 14 traces a curve which is almost parabolic in shape, particularly near the maximum. Gradient search techniques use iteration steps proportional to $\nabla_k$ as in Eq. (39).

$$C_{2_{k+1}} = C_{2_k} + \mu \nabla k \quad (39)$$

Where μ is a constant, a design parameter $$\nabla_k = \frac{\partial |V_L|}{\partial C_2} \bigg|_{C_2 = C_{2_k}} \quad (40)$$

Figure 15:
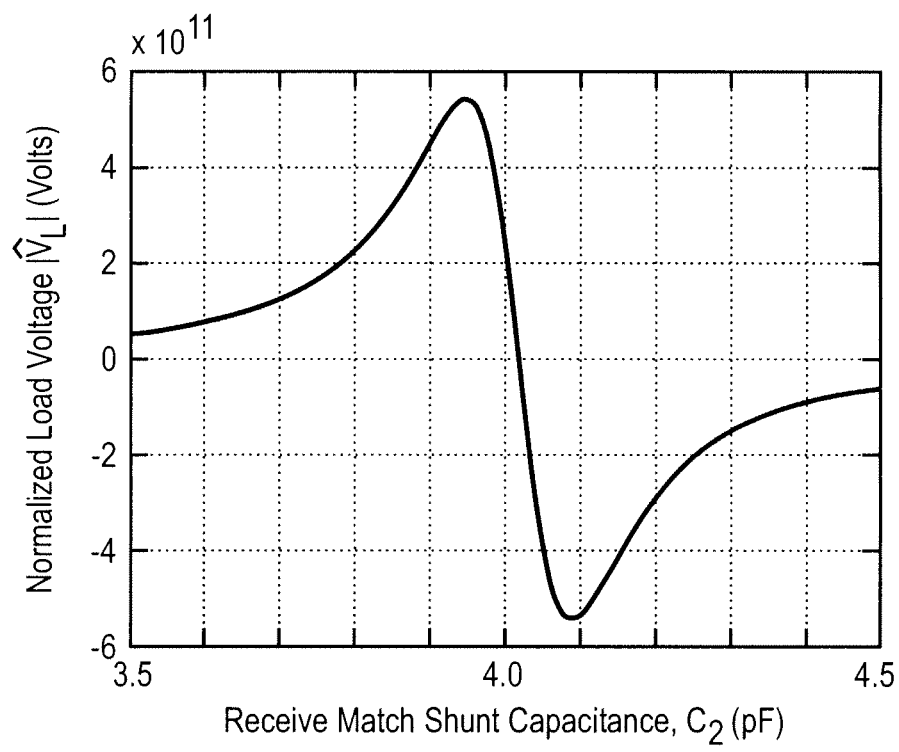

FIG. 15 however shows that $\nabla_k$ is not linear in C2, so $|V_L|$ is not a parabolic function of $C_2$. In fact $\nabla_k$ becomes very large near the optimum point and quickly transitions through zero at the optimum point so the popular stochastic gradient descent algorithm LMS would not be a stable. FIG. 15 does show that $|V_L|$ is a monotonically increasing function of $C_2$ for $C_2 < C_{2,opt}$ and a monotonically decreasing function of $C_2$ for $C_2 > C_{2,opt}$. If fixed step size iterations are used and the direction of iteration is chosen by the sign of $\nabla_k$ as illustrated in Eq. (41) then the output will tend to the desired value.

$$C_{2_{k+1}} = C_{2_k} + \mu \cdot sgn(\nabla_k) \quad (41)$$

The drawback of fixed step size adaptation is the difficulty in choosing an appropriate step size to achieve a satisfactory tradeoff between speed of convergence and accuracy. An improvement which will be readily applicable in the implementation is to use a hybrid of binary search and gradient search. The idea being to start with some maximum step size and iterate C2 by adding the step size to $C_2$ if $\nabla_k > 0$ or subtracting the step size from $C_2$ if $\nabla_k < 0$ at each iteration. When $\nabla_k$ changes sign the step size should be halved. This is the match adaptation algorithm we use and is summarized below.

$$\begin{aligned} &\text{if} \quad sgn(\nabla_k) = sgn(\nabla_k) \\ &\text{then} \quad \mu_k = \mu_{k-1} \\ &\text{else if} \quad sgn(\nabla_k) \neq sgn(\nabla_k) \\ &\text{then} \quad \mu_k = \frac{\mu_{k-1}}{2} \\ &\text{end} \quad C_{2_{k-1}} = C_{2_k} + \mu_k \cdot sgn(\nabla_k) \end{aligned} \quad (42)$$

The algorithm depends only on the sign of the gradient, not on the value of the gradient itself. Therefore there is no need to calculate the gradient value, calculating just the sign is easier and will save power and area.

Figure 16:
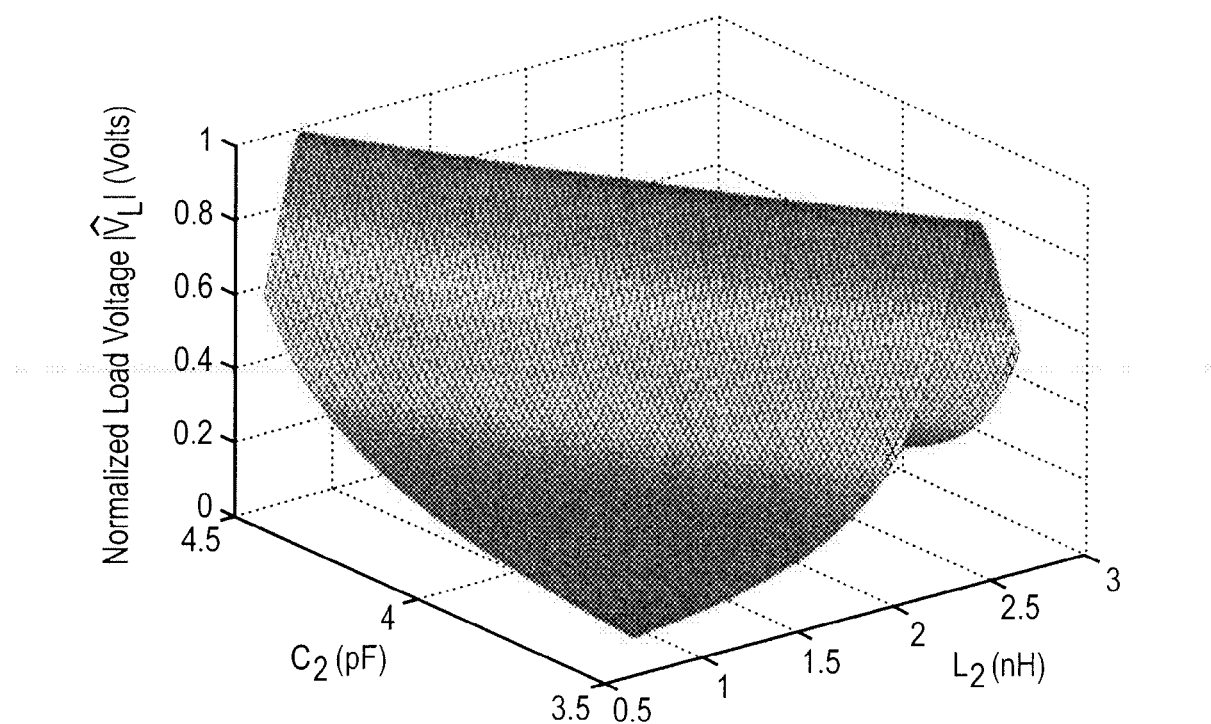
FIG. 16 shows a surface-plot of $|V_L|$ versus $(L_2, C_2)$.

A surface-plot of $|V_L|$ versus $(L_2, C_2)$ as shown in FIG. 16, the series inductance and shunt capacitance of the receive match, shows that there is only one degree of freedom. That is for a fixed value of one component in the match the other component can be varied to achieve the maximum $|V_L|$ and thus maximum power transfer. The transmit and receive matches are to first order independent and can be tuned separately. A similar argument as applied to the receive match can be applied to the transmit-side match. Therefore the complete link matching has two degrees of freedom which may be treated as independent, one in the transmit match and one in the receive match.

G. Tunable Match Implementation

It is easier to tune shunt capacitors than series inductors for a number of reasons. Firstly shunt elements can be just switched in or out with a single switch at either terminal whereas switching in/out a series element also requires switching out/in a short circuit in its place require more switches and control circuitry and increasing parasitics and area. Secondly switch parasitic capacitances can easily be absorbed in the capacitance of the shunt capacitors but cannot be absorbed by the inductors and thirdly varactors are readily manufacturable in CMOS but variable inductors are not. Primarily because of the first two reasons it was chosen to tune the shunt capacitance. The variable capacitance was realised as binary weighted capacitor array rather than a varactor because the control algorithm is implemented digitally and its output can feed directly to the switches in the binary weighted capacitor array to select the capacitance, if varactors were used a digital-to-analog converter would be needed between the control algorithm circuits and the varactor increasing power dissipation, area and complexity; a binary weighted array of MiM capacitors array displays much superior linearity to a MOS varactor and the frequency of operation is slow enough relative to the pass gate resistance and capacitor array time constant that charging delay is negligible.

Figure 17:
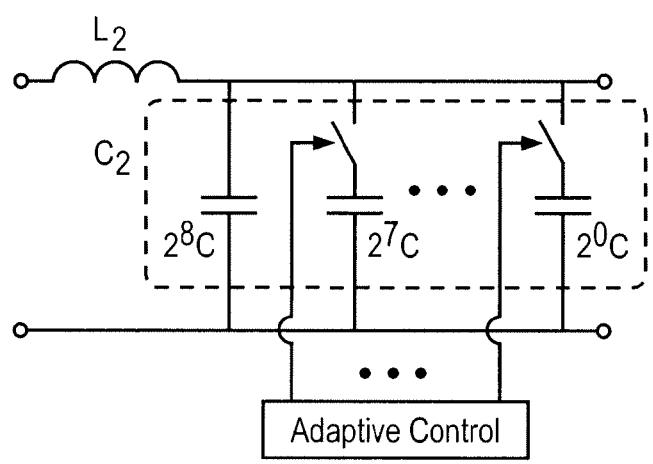
FIG. 17 shows an embodiment of a 9 element binary weighted capacitor array.

For the implementation, one embodiment of a 9 element binary weighted capacitor array was used, as shown in FIG. 17. Each of the capacitors in the array is selectable apart from the $2^8 C_{unit}$ capacitance which is permanently connected. At startup all of the switches are open and $C_2=3.7$ pF, ensuring that the 3-stage rectifier output$\geq 0.7$ V for all antennae separation from 7.2 mm to 19.1 mm. This voltage is used as the supply for the array switches. The sign of $\nabla_k$ is found by switching the smallest capacitance in and out of the array. No addition, multiplication or division operations are required, just a compare operation which simplifies the circuitry required and saves processing power and area. In this embodiment the capacitor array and digital control are implemented on chip but the adaptation algorithm is run off of the receive chip, though in other embodiments it is possible to have the adaptation algorithm on-chip as well. $C_2$ converges to the optimum value.

In the above embodiment, the adaptive matching used feedback from the receive IC to assist in providing the adaptive matching. This feedback is implemented as, in one embodiment, a configuration wherein the receive-side adaptive match circuit receives a particular tuned impedance from a tunable impedance from the transmit-side, and provides a feedback signal to the transmit-side adaptive match circuit, such that the feedback signal provides an indication of a gain of the power signal as received at the wireless power transmitter for a particular tuned impedance, and which the transmit-side adaptive-match circuit can then use to automatically adjust the impedance of the tunable impedance in order to increase a gain of the received power signal by the receiver. That this can be constantly monitored allows, in an environment of unknown transmission characteristics that change over time, sufficient power transfer throughout the period necessary for usage.

While such feedback is preferable, in another embodiment, particularly with the adaptive algorithm off-chip, it is possible to measure gains by incremental changes from the transmit-side, and converge to a preferable match without obtaining feedback from the receive-side.

Even without feedback the simultaneous conjugate matching technique is still useful if the link parameters (antenna alignment, range and inter-antennae medium) can be estimated reasonably accurately.

III. DC Conversion

When the link is simultaneously conjugate matched to the known source and typical load impedances we expect a voltage amplitude of approximately 0.75 V at the output of the match at the receiver for a 250 mW input power at the transmitter, the maximum input as discussed earlier. This 0.75 V 1 GHz signal must be converted to a usable DC to power the implanted IC.

A. Rectifier Design

A CMOS rectifier using diode connected MOSFETs with $V_{TH}=0.4$V would generate, after capacitive smoothing, an ideal output voltage $V_{DC}=0.35$V for an input amplitude $V_{IN}=0.75$V, dissipating more than half of the power delivered across the rectification diodes. Instead a synchronous self-driven rectifier is used as shown in FIG. 18(*a*). The basic operation is as follows: in the half cycle when node X is high relative to node Y, $M_0$ and $M_2$ are "on" and $M_1$ and $M_3$ are "off". The applied gate-source voltage may not be enough to turn the devices strongly on or off so the devices can be thought of as voltage dependent resistances as shown in as illustrated in FIG. 18(*b*). Provided $R_{OFF,N}$, $R_{OFF}$, $P \gg R_L$ current will be steered to the load through opposite transistor paths each half-cycle and an ideal rectified voltage of $$V_{REC} = \frac{R_L}{R_L + R_{ON}} V_{IN}$$

produced, where $R_{ON}=R_{ON,N}+R_{ON,P}$. To first order this design is more efficient than using diode-connected devices for rectification if the ideal voltage drop due to forward conduction loss, $$\frac{R_{ON}}{R_L + R_{ON}} V_{IN},$$

is less man $V_{TH}$.

The foregoing discussion idealizes the source as a square wave. However the source is sinusoidal resulting in additional loss mechanisms. Since the peak value of $V_{IN}$ is not much greater than $V_{TH}$, the "on" and "off" resistances are relatively similar in magnitude for a significant duration of each cycle as illustrated in the middle panel of FIG. 19. Simulated currents through each of transistors in FIG. 18(*a*) are illustrated in the bottom panel of FIG. 19. The large peaks correspond to current being delivered to the load as intended. In between these large bumps, in the nominally dead zone, as the input voltage falls below the DC output we see significant reverse currents through the "on" devices and the supposedly "off" devices shunt current away from the load.

Design choices affect these losses in order to design the most efficient rectifier. As W/L is increased $R_{OFF}$ and $R_{ON}$ decrease. Decreasing $R_{ON}$ reduces forward conduction loss, but decreasing $R_{OFF}$ increases reverse conduction and "off" state conduction loss. If we combine these two losses and plot the ratio of loss in the rectifier to power delivered to the load versus widths of the NMOS and PMOS devices we see a convex surface plot with a global optimum point. Therefore an optimum set of W/L exists which minimizes total loss. A slice through that curve is shown in FIG. 20 which shows that the optimum PMOS width is 4 µm for minimum length devices. Each rectifier stage, optimally sized, has a $V_{DROP}$=0.15 V for a 0.75 V amplitude input. Three stages are connected in a charge pump configuration to generate a 1.8 V DC output. The pumping capacitance is 1 pF, chosen to equal the output smoothing capacitance. Deep N-well isolation of the rectifier transistors whose bulk terminals are tied to their source terminals ensures that there is no degradation of voltage generated per stage due to body effect.

B. Rectifier Input Impedance

In order to design the match correctly it is important to know the source and load impedances. An off-the-shelf transmit driver is used and the source impedance is 50Ω. The load impedance is the input impedance of the loaded rectifier, $Z_{in,rect}$. Ideally $Z_{in,rect}$ would be independent of the rectifier and equal to the resistance the rectifier must drive, Eq. (43).

$$Z_{in,rect\ ideal} \approx R_L \quad (43)$$

However non-idealities such as the non-zero impedance of the rectifier itself, parasitic capacitances within the rectifier and finite smoothing capacitance at the rectifier output take on greater significance in this low-voltage, high-frequency design and considerably impact rectifier input impedance.

The pump capacitances, $C_P$ in FIG. 21, present impedances of j159Ω at the signal frequency, much smaller than both the on-resistance of the current steering rectifier cell and the load resistance and so can be approximated by short circuits. FIG. 21 shows that each transistor's gate connects to one input line and the transistor's source connects to the other input line. So each transistor adds a gate-source capacitance, $C_{gs}$, across the input terminals. In each rectifier cell, one NMOS and one PMOS are ON and one NMOS and one PMOS are OFF at any given time. $C_{gs}$ of the OFF devices is negligible. The ON transistors are in the triode region and so the $C_{gs}$,ON is approximately half of the gate-to-channel capacitance, $C_{gs}$. For the device sizes chosen each stage contributes $C_{gs,ON,NMOS}+C_{gs,ON,PMOS}=\frac{1}{2}(C_{gc,N}+C_{gc,P})\approx 8$ fF across the input terminals, totaling N/2 $(C_{gc,N}+C_{gc,P})$ where N=3 is the number of rectifier stages. In series with the load resistance we must place the on-resistance of each cell to account for conductive losses, N $(R_{on,N}+R_{on,P})$. Ideally the output smoothing capacitance, in parallel with the resistive load, would be infinite giving a purely dc output and hence the output smoothing capacitance would be irrelevant to the input impedance.

However the presence of output voltage ripple means that there is the loading is not purely resistive. This is a non-linear effect and the ripple frequency is twice that of the input frequency but we can crudely model it by considering the total charging and discharging at that node per input period. For a ripple peak-to-peak voltage of $V_{ripple}$ then the output capacitance charges up and discharges by $C_{smooth}V_{ripple}$ twice each input period corresponding to an aggregate charge change of $\Delta Q=2C_{smooth}V_{ripple}$ each input period. We want to model the shunting of current parallel to the load resistance and so this charging and discharging is modeled by a capacitance $C_{L,eq}=\Delta Q/\Delta V$ where $\Delta V=V_L=0.6V$ is the voltage across $R_L$. Therefore for ripple $V_{ripple}$=2 mV with a smoothing capacitance of $C_{smooth}$=1 pF, $$C_{L,eq} = \frac{2(1\ \text{pF})(2\ \text{mV})}{0.6\ \text{V}} = 6.7\ \text{fF}.$$

The input impedance can then be modeled as shown in FIG. 22 giving a second approximation to $Z_{in,rect}$ of $$Z_{in,rect} \approx \frac{1}{j\omega\frac{N}{2}(C_{gc,N}+C_{gc,P})} \left\| \left[ N(R_{on,N}+R_{on,P}) + \left( R_L \left\| \frac{1}{j\omega\frac{2V_{ripple}}{V_L}C_{smooth}} \right) \right] \right. \quad (44)$$

At 1 GHz Eq. (44) gives $Z_{in,rect}$=1917 j4795Ω which is equivalent to a resistance of 13.9 kΩ in parallel with a capacitance of 28.7 fF. This approximate model for the load impedance is used at the initial design phase and gives us some intuition as to how design choices affect $Z_{in,rect}$. After the initial design we estimate the input impedance through simulation as follows in which we approximate the input current as sinusoidal. The magnitude of the input impedance is calculated by dividing the peak-to-peak value of applied voltage by the peak-to-peak value of input current, $$|Z_{in,rect}| = \frac{V_{in,p-p}}{I_{in,p-p}},$$

while the phase of the input impedance is estimated by measuring the phase delay between applied voltage and input current, $\angle Z_{in,rect}=\angle(V_{in,p-p},I_{in,p-p})$. To further corroborate these estimates calculate the real part of $$Z_{in,rect}\ \text{by real}\left(\frac{1}{Z_{in,rect}}\right) = \frac{2P_{in,rect}}{|V_{in}|^2}.$$

Strictly speaking $Z_{in,rect}$ is a non-linear function of the voltage applied and so varies over the period. Simultaneous conjugate matching assumes that the load impedance is constant. $R_L$ is linear whereas N $(R_{on,N}+R_{on,P})$ varies with the applied voltage. Fortunately for a well designed rectifier $R_L>>N$ $(R_{on,N}R_{on,P})$ so $R_L+N$ $(R_{on,N}+R_{on,P})$ is approximately constant. The other nonlinear element in our model is $C_{L,eq}$ but the nonlinear variation is a small compared of the overall impedance. We match to the typical value of this impedance achieving near-maximum power transfer, demonstrating that, for the input waveform in question, the non-linearity can be neglected. The weakness of the nonlinearity is to be expected since the typical input impedance, $Z_{in,rect}$=13.9 kΩ∥28.7 fF, is dominated by the load impedance $R_L$=12 kΩ which is linear in parallel with N/2 $(C_{gc,N}+C_{gc,P})$=24 fF which is very weakly non linear.

C. Regulator

Regulator optimization is not the focus of this work but a regulator was needed to provided a stable 1.2V supply to some other devices on the die. A series regulator was used which incorporates two replica bias stages, FIG. 23. The first replica bias is used to generate the gate bias for the output stage, desensitizing the gate voltage to load switching. If the output stage current falls below approximately 8 µA the output voltage begins to rise, i.e. the load impedance becomes too large with respect to the replica bias. To overcome this problem a second replica bias and control loop maintains a minimum current of 15 µA through the output stage. Conceptually the loop tries to close the switch as the current falls below 20 µA and ensures an absolute minimum current of 15 µA.

IV. Measured Performance

A block diagram of an implemented embodiment is illustrated in FIG. 24. The power transmitter is implemented on a PCB incorporating a power amplifier and an adaptive match together with a 2 cm×2 cm transmit loop antenna. The power receiver consists of a 2 mm×2 mm receive loop antenna and the power receiving IC which includes adaptive match, rectifier and regulator. The transmit antenna is placed 1 cm above the tissue surface and the receiver implanted 15 mm deep in bovine muscle tissue with the two antennae axially aligned as illustrated in FIG. 25.

The power receiving IC was implemented in CMOS and bonded to the receive loop antenna with controlled bond wire length to realize the series inductance of the receive match. The receive match tunable capacitance, rectifier and regulator are all on chip. The gates and drivers which control the tunable capacitance were implemented on chip whilst the search algorithm was performed off-chip and the signals fed to the receiver chip in this embodiment of the device.

The rectifier and regulator output voltages were measured versus load impedance as the load impedance was varied form 2.4 kΩ to 36 kΩ and are plotted in FIG. 26 for transmit input power of 250 mW. The regulator output of 1.2V±1% is maintained as the current load varies from 15 µA to 120 µA. The rectifier and regulator output voltages measured versus implant depth for a load impedance of 12 kΩ are plotted in FIG. 27. The regulator output of 1.2V±1% is maintained as the range varies from 7.5 mm to 17 mm. The measured rectifier efficiency is 65%. The combined startup time of the rectifier and the regulator is 4 µs, dominated by the regulator.

In order to evaluate the adaptive match we consider a ±1 mm placement accuracy. First we ideally align the antenna, run the match adaptation and measure the rectifier output voltage, $V_{REC}$. Next we hold those match parameters fixed, misalign the antennae axially by 1 mm, increase the implantation depth of the receiver by 1 mm and measure $V_{REC}$ again. This corresponds to the voltage we would receive if we designed a static match for the ideal alignment but the realized link was 1 mm inaccurate axially and laterally. Finally we turn the match adaptation back on and measure $V_{REC}$ again. From those measured $V_{REC}$ we calculate the combined gain of the link and rectifier for each case. These are listed in Table IV.

TABLE IV

ADAPTATIVE MATCH PERFORMANCE.

| Link | Matching | Link Gain |
| --- | --- | --- |
| Ideal | for ideal link | −32.1 dB |
| Non-Ideal | for ideal link | −35.8 dB |
| Non-Ideal | for non-ideal link | −32.3 dB |

Without adaptive matching an implant placement accuracy of 1 mm and tissue thickness estimation accuracy of 1 mm we could lose up to 3.7 dB of the link gain. However the adaptive match boosts the link gain by 3.5 dB for ±1 mm misplacement, recovering almost all of the lost gain. The link gain numbers in Table IV are of the link and rectifier together, the total gain of the link, rectifier and regulator is −33.2 dB. The performance is summarised in Table V.

TABLE V

PERFORMANCE SUMMARY.

| | |
| --- | --- |
| Tx Antenna Size | 2 cm × 2 cm |
| Tx Power | 250 mW |
| Operating Frequency | 915 MHz or 1 GHz |
| Inter-Antenna Dielectric | 10 mm free space and 15 mm bovine muscle tissue |
| Rx Antenna Size | 2 mm × 2 mm |
| Technology | 0.13 µm CMOS |
| Area | 0.37 mm$^2$ |
| Startup Time | 4 µs |
| Rectifier Efficiency | 65% |
| Gain of Link, Rectifier and Regulator | −32.2 dB |
| DC Power Out | 140 µW @ 1.2 V |

Applications

The present invention can be applied to provide a remote power source for the operation of implantable devices such as cardiac rhythm management systems (for example, pacemaker and cardiac defibrillator), neurostimulators, drug delivery systems, and medical sensors (for example, blood glucose sensors.) The internal battery of those devices can then be removed. This will dramatically reduce the size of the implanted devices allowing more effective drug delivery and neurostimulation. For example implanted drug delivery systems can be located closer to the cancer cells.

The present invention can be applied to provide a "self-powered" data link to any implantable device. The data link can be used to remotely program the operation of the devices and retrieve information from the devices. This data link will not consume any power from the internal battery of the implantable devices. Thus, it will not affect the battery lifetime of the implantable devices. In addition, the present invention provides enough power not only for the data transmission but also support two-way encryption. This security measure will avoid hackers from breaking the normal operation of the implantable devices.

The present invention can also be applied to the embedding of security IDs inside medical pills such as prescription drugs. Power is delivered from the external transceiver (pharmacy pad) to the pill where a processor and related application programming performs encryption and authentication. This security ID can also be used for post-mismedication tracking. The external transceiver will track the security ID inside the body and check out the type of medicine that had been taken by patients.

Although the present invention has been particularly described with reference to embodiments thereof, it should be readily apparent to those of ordinary skill in the art that various changes, modifications and substitutes are intended within the form and details thereof, without departing from the spirit and scope of the invention. Accordingly, it will be appreciated that in numerous instances some features of the invention will be employed without a corresponding use of other features. Further, those skilled in the art will understand that variations can be made in the number and arrangement of components illustrated in the above figures. It is intended that the scope of the appended claims include such changes and modifications.

What is claimed is:

1. An apparatus for wireless power transmission within an environment of unknown transmission characteristics comprising:
- a wireless power transmitter, the wireless power transmitter including:
  - an adaptive match transmit circuit with a tunable impedance, which supplies a tunable impedance to a power signal having a frequency of at least 0.5 GHZ; and
  - a wireless transmitter; and
- a wireless power receiver, the wireless power receiver including:
  - multiple receive antennas configured to receive the transmitted power signal as a received power signal to maximize power transfer efficiency;
  - an adaptive match receive circuit, wherein the adaptive match receive circuit receives the received power signal, and is configured to match the tunable impedance, in dependence upon the environment of unknown transmission characteristics, to thereby increase a gain of the received power signal,
- wherein the wireless power transmitter and the wireless power receiver are disposed a distance apart that ranges between wavelength/100 to wavelength*100.

2. The apparatus according to claim 1 wherein the adaptive match receive circuit provides a feedback signal to the adaptive match transmit circuit, wherein the feedback signal provides an indication of a gain of the power signal as received at the wireless power transmitter for a particular tuned impedance.

3. The apparatus according to claim 1 wherein the wireless power transmitter includes a beam forming mechanism.

4. The apparatus according to claim 1 further including:
- an implant, wherein the wireless power receiver is attached to the implant
- a battery-less medical device attached to the implant; and
- a rectifier attached to the implant and electrically coupled between the wireless power receiver and the battery-less medical device, the rectifier creating a direct current from the power signal, which direct current powers the battery-less medical device.

5. The apparatus according to claim 4 further including a regulator disposed between the rectifier and the battery-less medical device, the regulator providing a regulated output power signal to the battery-less medical device.

6. The apparatus according to claim 4 further including an implicit feedback mechanism in which an external device senses presence of the implant to adapt to changing location of the implant, without requiring explicit feedback of information.

7. The apparatus according to claim 6 wherein the implicit feedback mechanism is a transceiver locator.

8. The apparatus according to claim 7 wherein the transceiver locator operates using a detected backscattered signal and provides a location estimate as an output.

9. The apparatus according to claim 4 further including a data link that remotely programs the medical device and which retrieves information from the medical device, the data link including an external transceiver and an internal transceiver.

10. The apparatus according to claim 9 wherein the data link supports two-way encryption.

11. The apparatus according to claim 1, further including:
- an implant, wherein the wireless power receiver is attached to the implant
- a medical device attached to the implant; and
- a rectifier attached to the implant and electrically coupled between the wireless power receiver and the battery-less medical device, the rectifier creating a direct current from the power signal, which direct current powers the medical device.

12. The apparatus according to claim 11 further including a data link that remotely programs the medical device and which retrieves information from the medical device, the data link including an external transceiver and an internal transceiver.

13. The apparatus according to claim 12 wherein the data link supports two-way encryption.

14. The apparatus according to claim 13 further including a battery for operation of the medical device, and wherein the data link does not use any power from the battery, but only the direct current from the rectifier.

* * * * *